US012760333B2

(12) United States Patent
Michel et al.

(10) Patent No.: US 12,760,333 B2
(45) Date of Patent: Oct. 13, 2026

(54) PROCESS FOR HIGH YIELD, HIGH PURITY EXTRACTION OF RUBBER FROM NON-*HEVEA* SOURCES

(71) Applicant: Ohio State Innovation Foundation, Columbus, OH (US)

(72) Inventors: Frederick Michel, Wooster, OH (US); David Alexander Ramirez Cadavid, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 241 days.

(21) Appl. No.: 18/577,486

(22) PCT Filed: Jul. 1, 2022

(86) PCT No.: PCT/US2022/073364
§ 371 (c)(1),
(2) Date: Jan. 8, 2024

(87) PCT Pub. No.: WO2023/283532
PCT Pub. Date: Jan. 12, 2023

(65) Prior Publication Data

US 2024/0368634 A1 Nov. 7, 2024

Related U.S. Application Data

(60) Provisional application No. 63/219,503, filed on Jul. 8, 2021.

(51) Int. Cl.
*C12P 5/00* (2006.01)
*C08C 2/06* (2006.01)

(52) U.S. Cl.
CPC ................ *C12P 5/007* (2013.01); *C08C 2/06* (2013.01)

(58) Field of Classification Search
CPC ............... C12P 5/007; C08C 1/02; C08C 2/00
See application file for complete search history.

(56) References Cited

U.S. PATENT DOCUMENTS 2,399,156 A 4/1946 Stamberger et al.
7,540,438 B2 6/2009 Buranov
9,346,924 B2 5/2016 Wade et al.
9,567,457 B2 2/2017 Huang et al.
2016/0304830 A1* 10/2016 Cornish .................. C12P 19/14
2019/0233595 A1 8/2019 Hruschka et al.
2021/0087300 A1 3/2021 Van Dijk et al.

OTHER PUBLICATIONS

International Searching Authority (ISA/US). International Search Report and Written Opinion. PCT Application No. PCT/US2022/073364. Issued on Oct. 6, 2022. 8 pages.

Eskew. Natural rubber from Russian dandelions. 856-864. India Rubber World. Web. Jan. 1946. Rubber-Recovery Process: Paragraph 1 on p. 858. 9 pages.

L. Xu, C. Huang, M. Luo, W. Qu, H. Liu, Z. Gu, L. Jing, G. Huang, J. Zheng, A rheological study on non-rubber component networks in natural rubber, RSC Adv. 5 (2015) 91742-91750.

S. Amnuaypornsri, J. Sakdapipanich, Y. Tanaka, Highly purified natural rubber by saponification of latex: analysis of green and cured properties, J. Appl. Polym. Sci. 118 (2010) 3524-3531.

S. Amnuaypornsri, J. Sakdapipanich, S. Toki, B.S. Hsiao, N. Ichikawa, Y. Tanaka, Strain-induced crystallization of natural rubber: effect of proteins and phospholipids, Rubber Chem. Technol. 81 (2008) 753-766.

K. Cornish, Alternative natural rubber crops: why should we care? Technol. Innov. 18 (2017) 245-256.

J.B. van Beilen, Y. Poirier, Guayule and Russian dandelion as alternative sources of natural rubber, Crit. Rev. Biotechnol. 27 (2007) 217-231.

J.B. Van Beilen, Y. Poirier, Production of renewable polymers from crop plants, Plant J. 54 (2008) 684-701.

Ahrends, P.M. Hollingsworth, A.D. Ziegler, J.M. Fox, H. Chen, Y. Su, J. Xu, Current trends of rubber plantation expansion may threaten biodiversity and livelihoods, Glob. Environ. Change 34 (2015) 48-58.

K. Cornish, S.K. McNulty, N. Amstutz, A.M. Chanon, S. Walker, M.D. Kleinhenz, A.R. Miller, J.G. Streeter, S.L. Kopicky, Temporal diversity of *Taraxacum kok-saghyz* plants reveals high rubber yield phenotypes, Biodiversitas 17 (2016) 847-856.

M. Kreuzberger, T. Hahn, S. Zibek, J. Schiemann, K. Thiele, Seasonal pattern of biomass and rubber and inulin of wild Russian dandelion (*Taraxacum koksaghyz* L. Rodin) under experimental field conditions, Eur. J. Agron. 80 (2016) 66-77.

M. Arias, J. Herrero, M. Ricobaraza, M. Hern'andez, E. Ritter, Evaluation of root biomass, rubber and inulin contents in nine *Taraxacum koksaghyz* Rodin populations, Ind. Crops Prod. 83 (2016) 316-321.

D.A. Ramirez-Cadavid, K. Cornish, F.C. Michel Jr., *Taraxacum kok-saghyz* (TK): compositional analysis of a feedstock for natural rubber and other bioproducts, Ind. Crops Prod. 107 (2017) 624-640.

M. Arias, M. Hernandez, N. Remondegui, K. Huvenaars, P. van Dijk, E. Ritter, First genetic linkage map of *Taraxacum koksaghyz* Rodin based on AFLP, SSR, COS and EST-SSR markers, Sci. Rep. 6 (2016) 31031.

Stolze, A. Wanke, N. van Deenen, R. Geyer, D. Prüfer, C.S. Gronover, Development of rubber-enriched dandelion varieties by metabolic engineering of the inulin pathway, Plant Biotechnol. J. 15 (2017) 740-753.

(Continued)

*Primary Examiner* — Tekchand Saidha
(74) *Attorney, Agent, or Firm* — Meunier Carlin & Curfman LLC

(57) ABSTRACT

The present disclosure provides for a method of purifying rubber from a plant that naturally produces rubber, the method including: a) contacting plant material with hot water or a dilute basic aqueous solution, thereby forming a plant material composition with a concentration of 3% or less of water extractable materials by weight and an inulin-containing composition; b) separating the plant material composition from the inulin-containing composition; c) pebble milling the plant material composition in the presence of enzymes; d) centrifuging the product of step c) to separate rubber from other material; and e) removing the rubber. Also provided herein is a product that can be obtained by any of the processes disclosed herein.

17 Claims, 13 Drawing Sheets

(56) References Cited

OTHER PUBLICATIONS

Y. Ikeda, P. Junkong, T. Ohashi, T. Phakkeeree, Y. Sakaki, A. Tohsan, S. Kohjiya, K. Cornish, Strain-induced crystallization behaviour of natural rubbers from guayule and rubber dandelion revealed by simultaneous time-resolved WAXD/ tensile measurements: indispensable function for sustainable resources, RSC Adv. 6 (2016) 95601-95610.
S. Musto, V. Barbera, M. Maggio, M. Mauro, G. Guerra, M. Galimberti, Crystallinity and crystalline phase orientation of poly(1,4-cis-isoprene) from Hevea brasiliensis and Taraxacum kok-saghyz, Polymers for Advanced Technologies, (2016) n/a-n/a.
D.A. Ramirez-Cadavid, K. Cornish, U. Hathwaik, R. Kozak, C. McMahan, F.C. Michel Jr., Development of novel processes for the aqueous extraction of natural rubber from Taraxacum kok-saghyz (TK), J. Chem. Technol. Biotechnol. 94 (2019) 2452-2464.
R.K. Eskew, Natural rubber from russian dandelion, Rubber Chem. Technol. 19 (1946) 856-864.
D.A. Ramirez-Cadavid, S. Valles-Ramirez, K. Cornish, F.C. Michel Jr., Simultaneous quantification of rubber, inulin, and resins in Taraxacum kok-saghyz (TK) roots by sequential solvent extraction, Ind. Crops Prod. 122 (2018) 647-656.
Limayem, S.C. Ricke, Lignocellulosic biomass for bioethanol production: current perspectives, potential issues and future prospects, Prog. Energy Combust. Sci. 38 (2012) 449-467.
S. Kim, M.T. Holtzapple, Effect of structural features on enzyme digestibility of corn stover, Bioresour. Technol. 97 (2006) 583-591.
R.A. Silverstein, Y. Chen, R.R. Sharma-Shivappa, M.D. Boyette, J. Osborne, A comparison of chemical pretreatment methods for improving saccharification of cotton stalks, Bioresour. Technol. 98 (2007) 3000-3011.
Kim, J.-I. Han, Optimization of alkaline pretreatment conditions for enhancing glucose yield of rice straw by response surface methodology, Biomass Bioenergy 46 (2012) 210-217.
E.M. Karp, B.S. Donohoe, M.H. O'Brien, P.N. Ciesielski, A. Mittal, M.J. Biddy, G.T. Beckham, Alkaline pretreatment of corn stover: bench-scale fractionation and stream characterization, ACS Sustain. Chem. Eng. 2 (2014) 1481-1491.
B.L. Johnson, Effect of molecular-weight distribution on physical properties of natural and synthetic polymers, Rubber Chem. Technol. 21 (1948) 654-666.
T. Gao, R. Xie, L. Zhang, H. Gui, M. Huang, Use of rubber process analyzer for characterizing the molecular weight parameters of natural rubber, Int. J. Polym. Sci. 2015 (2015), 517260.
D.T. Gentekos, R.J. Sifri, B.P. Fors, Controlling polymer properties through the shape of the molecular-weight distribution, Nature Reviews, Materials 4 (2019) 761-774.
B. Westall, The molecular weight distribution of natural rubber latex, Polymer 9 (1968) 243-248.
Subramaniam, Gel permeation chromatography of natural rubber, Rubber Chem. Technol. 45 (1972) 346-358.
R.P. Overend, E. Chornet, J.A. Gascoigne, Fractionation of lignocellulosics by steam-aqueous pretreatments, Philos. Trans. R. Soc. Lond. Ser. A Math. Phys. Sci. 321 (1987) 523-536.
H.L. Chum, D.K. Johnson, S.K. Black, R.P. Overend, Pretreatment-catalyst effects and the combined severity parameter, Appl. Biochem. Biotechnol. 24 (1990) 1.
F.J. Lu, S.L. Hsu, A vibrational spectroscopic analysis of the structure of natural rubber, Rubber Chem. Technol. 60 (1987) 647-658.
S. Rolere, S. Liengprayoon, L. Vaysse, J. Sainte-Beuve, F. Bonfils, Investigating natural rubber composition with Fourier Transform Infrared (FT-IR) spectroscopy: a rapid and non-destructive method to determine both protein and lipid contents simultaneously, Polym. Test. 43 (2015) 83-93.
M. García-Torreiro, M.Á. Pallín, M. López-Abelairas, T.A. Lu-Chau, J.M. Lema, Alkali treatment of fungal pretreated wheat straw for bioethanol production, Bioethanol 2 (2016).
E.M. Karp, M.G. Resch, B.S. Donohoe, P.N. Ciesielski, M.H. O'Brien, J.E. Nill, A. Mittal, M.J. Biddy, G.T. Beckham, Alkaline pretreatment of switchgrass, ACS Sustain. Chem. Eng. 3 (2015) 1479-1491.
S. Toki, C. Burger, B.S. Hsiao, S. Amnuaypornsri, J. Sakdapipanich, Y. Tanaka, Multi-scaled microstructures in natural rubber characterized by synchrotron X-ray scattering and optical microscopy, POLB J. Polym. Sci. Part B Polym. Phys. 46 (2008) 2456-2464.
Sakdapipanich, P. Rojruthai, Molecular structure of natural rubber and its characteristics based on recent evidence, biotechnology in: R. Sammour (Ed.) Molecular Studies and Novel Applications for Improved Quality of Human Life, InTech2012.
International Preliminary Report on Patentability dated Jan. 18, 2024.

* cited by examiner

| Tensile Properties | TSR20 | EZ | EZ+ Acid | EZ+ Base |
|---|---|---|---|---|
| M200 (psi) | 6.9 | 6.6 | 6.6 | 5.5 |
| Tensile (psi) | 28.17 | 23.56 | 24.14 | 24.2 |
| Peak Elongation (%) | 567 | 554 | 548 | 583 |

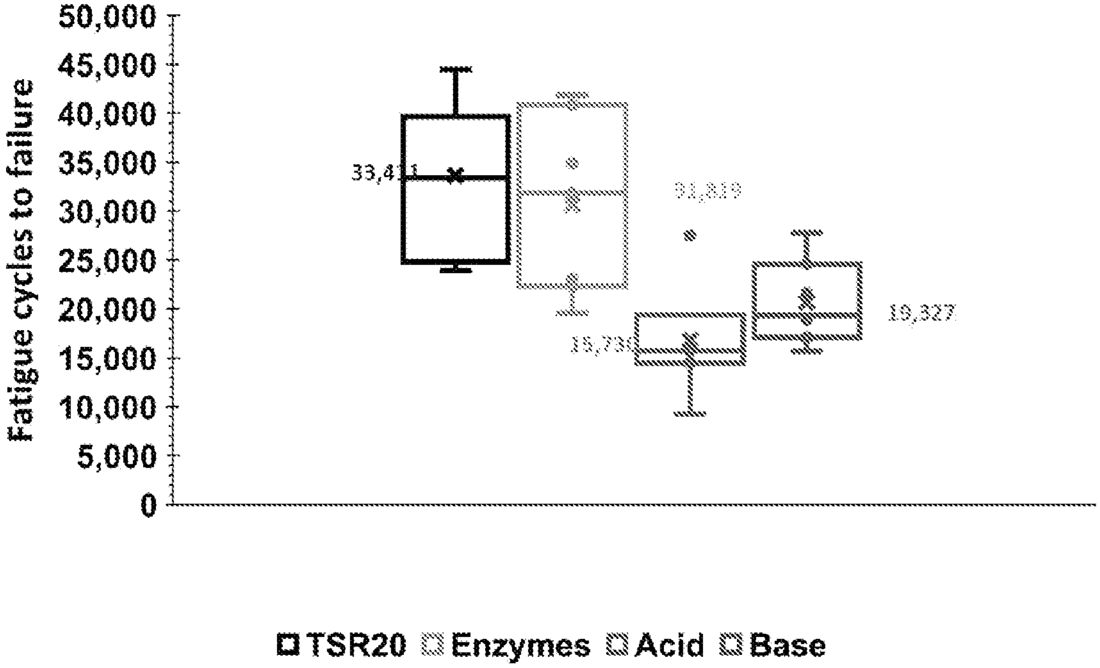
FIG. 10
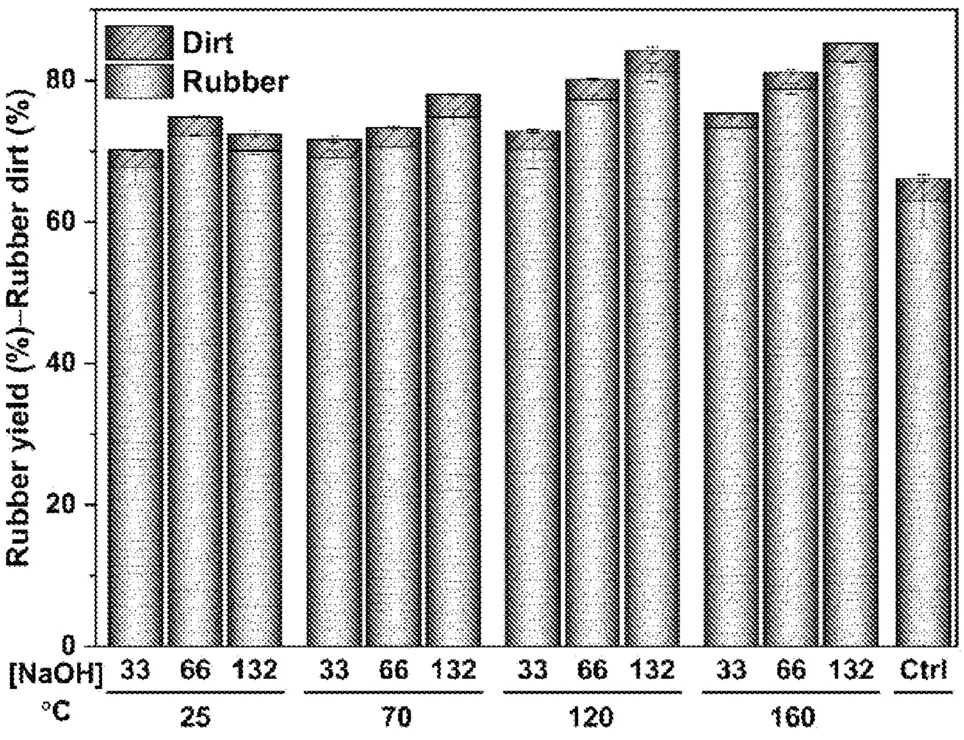

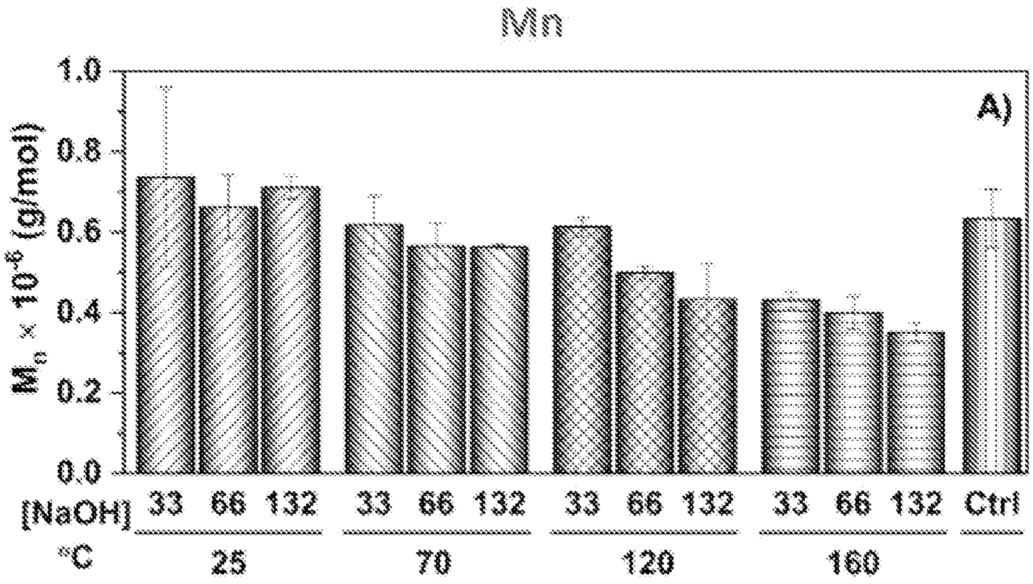
FIG. 12
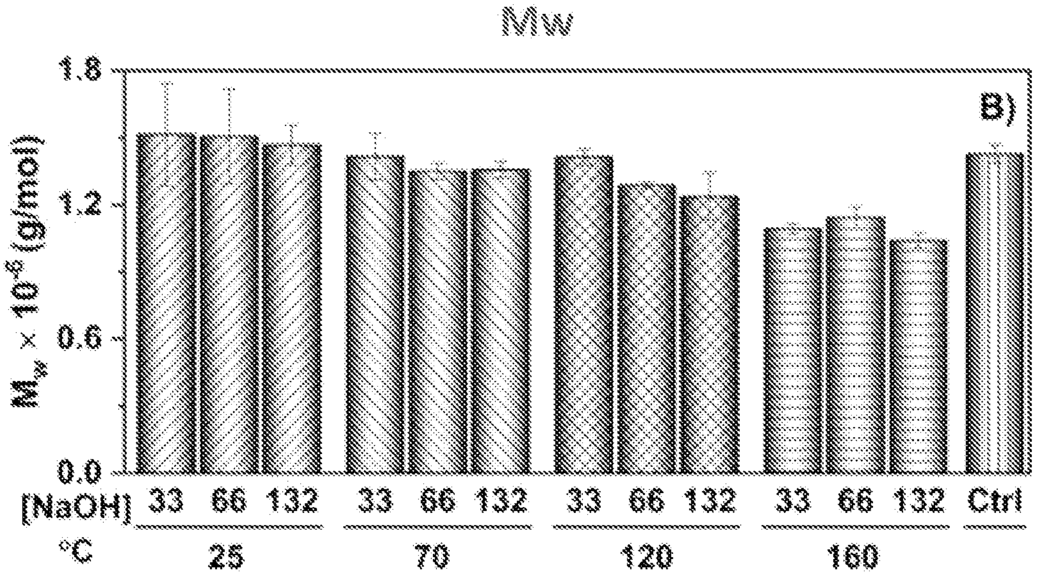

PROCESS FOR HIGH YIELD, HIGH PURITY EXTRACTION OF RUBBER FROM NON-*HEVEA* SOURCES

CROSS-REFERENCE TO RELATED APPLICATIONS

This application is a national stage application filed under 35 U.S.C. § 371 of PCT/US2022/073364 filed Jul. 1, 2022, which claims the benefit of priority to U.S. Patent Application No. 63/219,503, filed on Jul. 8, 2021, the disclosure of which is expressly incorporated by reference herein in its entirety.

GOVERNMENT SUPPORT CLAUSE

This invention was made with government support under grant or contract number 20181000828571 awarded by the USDA National Institute of Food and Agriculture. The government has certain rights in the invention.

BACKGROUND

Due to international concerns over future limited supplies of natural rubber, alternative sources are being developed. An alternative source of natural rubber to that produced from Rubber Trees (*Hevea brasiliensis*) is rubber produced by certain dandelion species such as *Taraxacum kok saghyz, T. brevicorniculatum* and *T. officianales*. This rubber exists in various parts of the plant, but is concentrated in the roots. The roots contain from 2% to 20% rubber and 10% to 50% inulin, a carbohydrate used as a food additive or source of fermentable sugars, on a dry weight basis. (See FIG. 1.)

A process for extracting the inulin and rubber, hereby referred to as the Eskew process, was developed in the 1940's by the USDA. This process starts with dried roots which are then roller milled and then extracted with hot water (>80° C.) using multistage cross current or counter current extraction to extract inulin and other water soluble constituents. The water extracted roots are then pebble milled to agglomerate the rubber and remove and pulverize the root skin. The milled root skin material has a particle size of less than 1 mm and is also known as bagasse. The rubber is separated from the bagasse by flotation.

The floated rubber is then screen separated and milled a second time to remove residual root material. The rubber from secondary milling is screen separated, washed, and blocked.

The Eskew process results in rubber at a low yield (<60%) that has a high level (>10%) of impurities or "dirt" as defined by ASTM D1278. The impurities are cell wall components that remain attached to the rubber. It requires organic solvent purification to yield high purity rubber. The Eskew process also requires two stages of pebble milling.

Enzymatic processes for *Taraxacum kok-saghyz* (TK) rubber extraction have been developed that digest the root skin to improve yield and purity in air lift or similar reactor configurations. However, they require the addition of water to form a slurry and long incubation times (24 to 48 h) requiring large tanks and high capital costs and the resulting rubber lacks sufficient purity.

Natural rubber (NR) is an essential biomaterial consisting of cis-1,4-polyisoprene and other minor components (Xu et al., 2015; Amnuaypornsri et al., 2010; Amnuaypornsri et al., 2008) that are used in countless automotive, medical, industrial and consumer products (Cornish, 2017; Van Beilen et al., 2007). NR has unique properties that are superior to those of synthetic rubber (Van Beilen et al., 2008). The para rubber tree, *Hevea brasiliensis*, cultivated primarily in Asian-Pacific countries, is the source of nearly all of the world's NR (Ahrends, et al., 2015). However, rising demand, price instability, climate change, labor costs, displacement by other crops, disease, and the 5-7 years required for new rubber trees to be first tapped, threaten its availability (Cornish, 2017; Ahrends, et al., 2015).

A variety of processes have been used to extract NR from TK roots including solvent extraction (Huang et al., 2015), wet milling (Ramirez-Cadavid et al., 2019; Eskew, 1946), milling coupled with alkaline purification (Stamberger et al., 1946), dry milling (Buranov, 2009), enzymatic digestion (Ramirez-Cadavid et al., 2019; Wade et al., 2013), and alkaline pretreatment plus enzymatic hydrolysis (Ramirez-Cadavid et al., 2019). Organic solvent extraction of TK NR (Huang et al., 2015) is an effective method but environmental, cost, and safety issues limit its usefulness, and it is reliant on unsustainable petroleum derived solvents. Additionally, the organic solvent-based extraction is slow and has a low yield due to gel formation and TK NR's high molecular weight that passes slowly through plant cell walls (Buranov et al., 2009). The use of heat and pressure to accelerate and increase the rate of solvent extraction degrades rubber quality (Ramirez-Cadavid et al., 2019; Ramirez-Cadavid et al., 2018).

What is needed in the art is a process that further improves yield and purity of the rubber, reduces the need to add water to prepare a slurry, and can speed up the process of extracting rubber. The method and products described herein address these and other needs.

SUMMARY

In accordance with the purposes of the disclosed materials and methods, as embodied and broadly described herein, the present disclosure relates to a method of purifying rubber and products made thereof.

Thus, in one aspect, provided herein is a method of purifying rubber from a plant that naturally produces rubber, the method including: a) contacting plant material with hot water or a dilute basic aqueous solution, thereby forming a plant material composition with a concentration of 3% or less of water extractable materials by weight and an inulin-containing composition; b) separating the plant material composition from the inulin-containing composition; c) pebble milling the plant material composition in the presence of enzymes; d) centrifuging the product of step c) to separate rubber from other material; and e) removing the rubber.

In an additional aspect, provided herein is a product that can be obtained by any of the processes disclosed herein.

The rubber-producing dandelion, *Taraxacum kok-saghyz* (TK), is an attractive alternative source of NR (Cornish et al., 2016; Kreuzberger et al., 2016; Arias et al., Evaluation of root biomass, 2016; Ramirez-Cadavid et al., 2017; Arias et al., First genetic linkage map, 2016; Stolze et al., 2017). TK NR's composition, molecular characteristics, and mechanical properties are similar to those of Hevea NR, and it can be used as a direct replacement in most applications. It is also amenable to modern agricultural methods and can yield rubber in a single growing season (Ikeda et al., 2016; Musto et al., 2016; Ramirez-Cadavid et al., 2019), Natural rubber usually exists within roots of TK plants at concentrations of less than 10% on a dry weight basis, though plants with a concentration greater than 10% have been identified. (Ramirez-Cadavid et al., 2017).

TK NR extraction by wet milling is an aqueous process wherein roots are first extracted in hot water to remove inulin, proteins, and other compounds, then pebbled-milled in aqueous media to physically separate root components and agglomerate the rubber (Eskew, 1946). About 60% of the NR in the roots is recoverable using this process but the rubber contains high levels of impurities (>11% of residual root tissue of a particle size >0.45 μm) that are detrimental to rubber performance (Ramirez-Cadavid et al., 2019; Stamberger et al., 1946; Baranwal et al., 2001; ASTM, 2015). Combining this approach with enzymatic hydrolysis using cellulase, hemicellulase, protease and/or pectinase increases TK NR yield to more than 70% and reduces impurities to less than 3% by hydrolyzing root structural polysaccharides (Ramirez-Cadavid et al., 2019). The use of an alkaline or acid pretreatment prior to enzymatic hydrolysis solubilizes the root tissue further, improving rubber yield (>80%) and increasing rubber purity to >98.5% (Ramirez-Cadavid et al., 2019). The effect of this pretreatment on the quality of the rubber can very, but depends on the severity of the pretreatment.

Alkaline pretreatment has been shown to solubilize and redistribute lignin, facilitating enzymatic saccharification of plant cell wall structural carbohydrates (Limavem et al., 2012; Kim et al., 2006). Previous studies have found that alkaline loading rate and pretreatment temperature are critical parameters for biomass pretreatment (Silverstein et al., 2007; Kim et al., 2012; Karp et al., 2014).

The method disclosed herein (also referred to as PENRA V) involves roller milling (see FIGS. 4A-4B), chopping, and/or sieving dried TK roots, followed by multistage hot water extraction of inulin/protein and other water-soluble components. The water-extracted roots are separated from the inulin/protein extract and then incubated with cell wall modifying enzymes in a pebble millor ball mill or any device capable of reducing the size of the water extracted roots by impact/shear/friction to hydrolyze, mill and remove the remaining root solids and release rubber.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

FIG. 7A shows the rubber yield with three different kinds of pretreatment: no pretreatment, acid pretreatment, and base pretreatment and FIG. 7B shows the rubber yield with three different kinds of pretreatment: no pretreatment, acid pretreatment, and base pretreatment.

FIG. 8 shows data for TK rubber extracted using base and acid pretreatment and enzymes, and data for Hevea NR SMR E.

FIG. 10 shows the results of an extension cycling fatigue test for compounded Hevea TSR 20, enzymes, acid, and base.

FIG. 11 shows rubber yield and purity. More specifically, FIG. 11 discloses the rubber yield % and rubber dirt % for samples pretreated at temperatures of 25° C., 70° C., 120° C., and 160° C., and with NaOH concentrations of 0, 33 mg NaOH/g dry roots, 66 mg NaOH/g dry roots, and 132 mg NaOH/g dry roots.

FIG. 12 shows the number average molecular weight (g/mol) of exemplary rubber after pretreatment at 25° C., 70° C., 120° C., and 160° C., with NaOH concentrations of 0, 33 mg NaOH/g dry roots, 66 mg NaOH/g dry roots, and 132 mg NaOH/g dry roots.

FIG. 13 shows the weight average molecular weight (g/mol) of exemplary rubber after pretreatment at 25° C., 70° C., 120° C., and 160° C., and NaOH concentrations of 0, 33 mg NaOH/g dry roots, 66 mg NaOH/g dry roots, and 132 mg NaOH/g dry roots.

DETAILED DESCRIPTION

Figure 1:
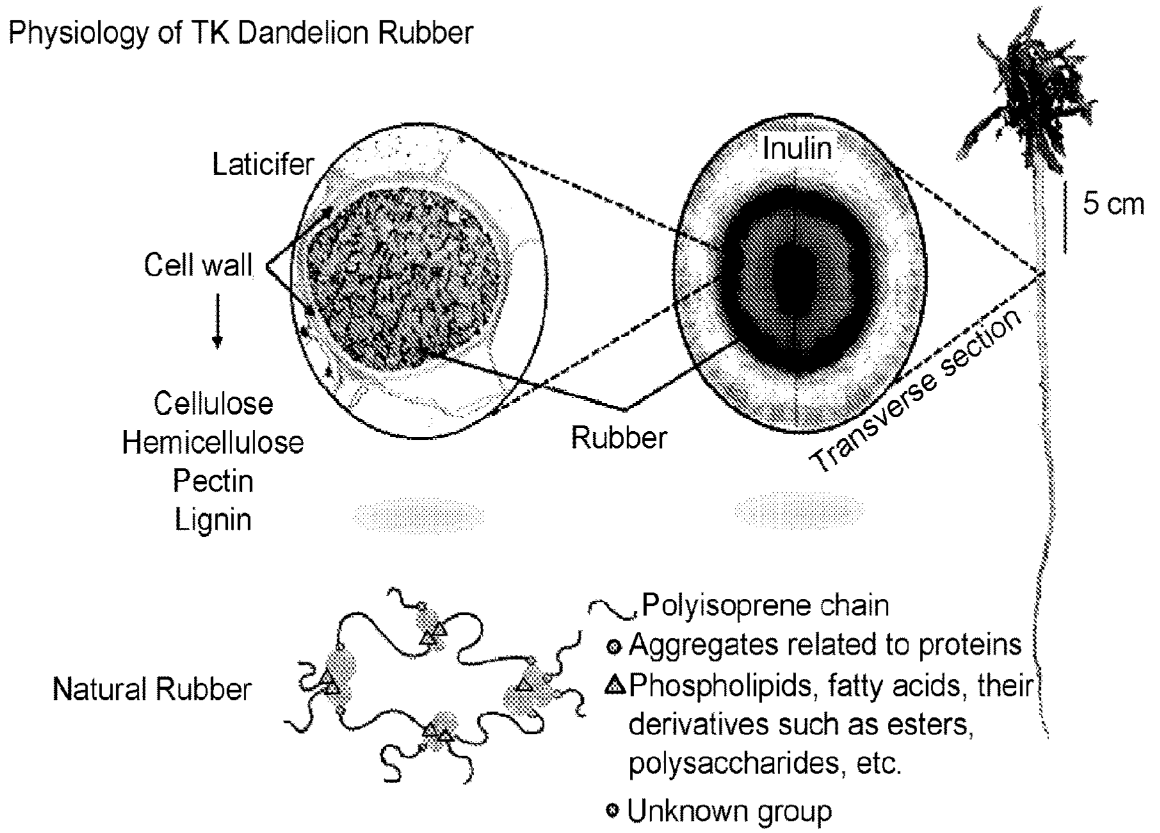
FIG. 1 shows the physiology of a transverse section of exemplary TK dandelion rubber. The physiology includes inulin, rubber, and laticifers, which further include a cell wall made up of cellulose, hemicellulose, pectin, and lignin.
Figure 2:
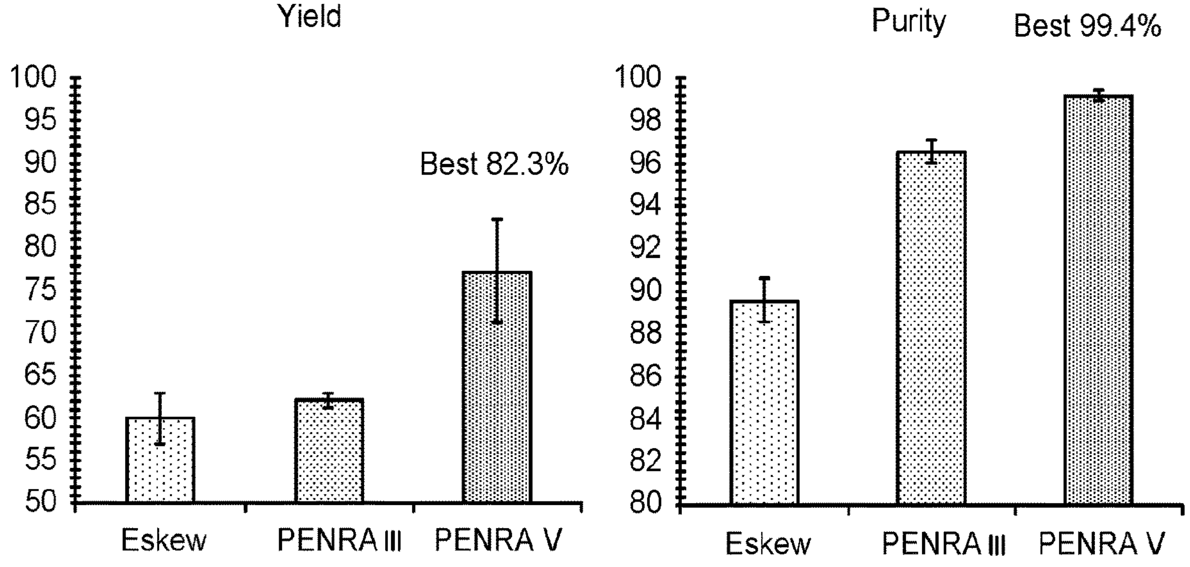
FIG. 2 shows a comparison of rubber extraction methods. More specifically, the figure compares yield and purity of rubber between three different methods: Eskew, PENRA III, and PENRA V. PENRA V performed best regarding both yield and purity.

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Terminology

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "0.1% to 5%" should be interpreted to include not only the explicitly recited values of 0.1% to 5%, but also include individual values (e.g., 1%, 2%, 3%, and 4%) and the sub-ranges (e.g., 0.5% to 1.1%; 5% to 2.4%; 0.5% to 3.2%, and 0.5% to 4.4%, and other possible sub-ranges) within the indicated range.

As used herein, "purify" refers to physically or chemically separating a substance of interest from other substances. More specifically as disclosed herein, purify refers to isolating rubber from a plant that naturally produces rubber and removing non-rubber substances from the rubber. In some embodiments, the rubber can be purified to greater than 0% rubber, greater than 20% rubber, greater than 40% rubber, greater than 60% rubber, or greater than 80% rubber. In further embodiments, the rubber can be purified to from 0% to 20%, 20% to 40%, 40% to 60%, 60% to 80%, or 80% to 100%. In certain embodiments, the rubber can be purified to from 50% to 60%, 60% to 70%, 70% to 80%, 80% to 90%, or 90% to 100%.

Rubber includes polymers of the organic compound isoprene. (See FIG. 1.) In some embodiments, rubber can include cis-1,4-polyisoprene. Rubber can include natural rubber as well as synthetic rubber. The types of polyisoprenes that can be used as natural rubbers are classified as elastomers. Natural rubber can be harvested from trees that produce rubber and can be used extensively across many applications and products. Natural rubber can come from a variety of plants, including, but not limited to, the Amazonian rubber tree, Congo rubber, dandelion, rubber fig, and the Panama rubber tree.

As used herein, hot water refers to water with a temperature from 200° F. to 212° F. In some embodiments, the temperature is from 200"F to 202° F., 202° F. to 204'F, 204"F to 206"F, 206° F. to 208° F., 208° F. to 210° F., or 210° F. to 212° F.

A dilute basic aqueous solution refers to an aqueous solution with a pH from 7 to 14 and an amount of solute that is dissolved in a comparatively larger amount of solvent. By "dilute" is meant that less than 100% of the solution is composed of the solute. For example, the solute can comprise 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, or 0.99% of the solution, or any amount in between, below, or above this amount. In another embodiment, the solute can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the solution, or any amount in between, below, or above, up to but not including 100%.

As used herein, "extract" refers to the process of isolating a substance from surrounding materials that are not of interest.

Inulin is a polysaccharide found in the roots or tubers of various plants. Plants that contain inulin include, but are not limited to, agave, banana, chicory, coneflower, and dandelion. Inulin can serve as a food additive or source of fermentable sugars.

Enzymes are proteins that act as catalysts in living organisms and can regulate the rate at which chemical reactions proceed without being altered in the process. Enzymes include, but are not limited to, pectinase, proteases, cellulase, and hemicellulase. Pectinase enzymes are in a group of enzymes that break down pectin, a polysaccharide found in plant cell walls, through hydrolysis, transelimination, and deesterification reactions. Cellulase enzymes are produced by microorganisms and specifically target cellulose to produce glucose. Cellulase can be produced by fungi, bacteria, archaea, and protozoans. Hemicellulase enzymes break down hemicellulose, which is a major component of plant cell walls. Hemicellulase can breakdown hemicellulose, which is a polymer of galactose, xylose, mannose, glucose and arabinose monomers, via hydrolysis. Enzymes can be used in combination or individually and one of skill in the art will understand the amount and method of using the enzymes as described herein.

As used herein, breaking down refers to the reduction in size of a substance, which can be accomplished via pebble milling, enzymes, or screening, for example.

A buffer is a solution that can resist pH change upon the addition of acidic or basic components. Buffers can neutralize small amounts of added acid or base, thus maintaining a relatively stable pH in the solution. Buffers can include a weak acid and a salt derived from that weak acid, or a weak base plus a salt derived from a weak base. More specifically, this can include acetic acid and sodium acetate, or ammonia and ammonium chloride.

Figure 3A:
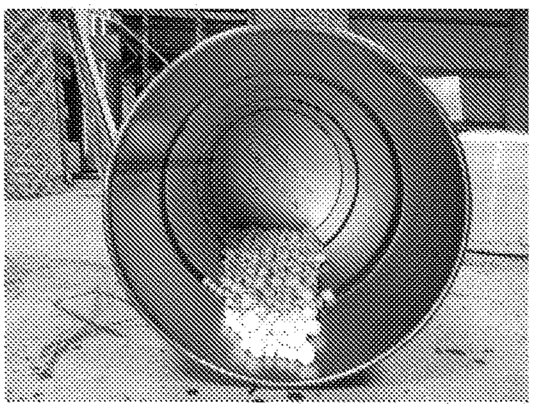
FIGS. 3A-3B show (FIG. 3A) an exemplary pilot scale process using a 10 gallon barrel with ceramic grinding media for mixing and (FIG. 3B) the same 10 gallon drum containing grinding media with 4.01 kg of inulin extracted TK roots on a dry weight basis.
Figure 3B:
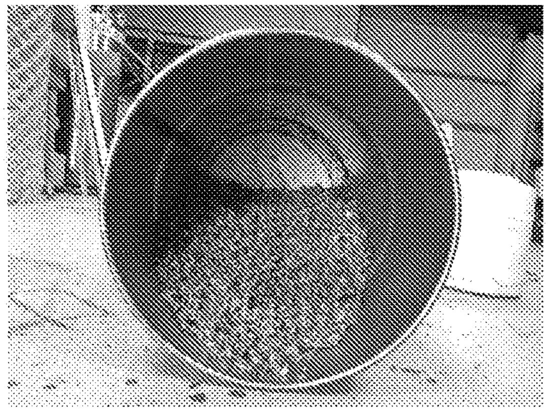

Mechanical separation includes, but is not limited to, separation methods such as filtration, sedimentation, centrifugation, screening, milling, chopping, or sieving. Filtration is a separation technique used to separate the components of a mixture containing an undissolved solid in a liquid. Filtration can be performed at high or low temperatures, using gravity or applying a vacuum, using a Buchner, Hirsch, or simple glass funnel. High pressure can also be used in filtration to force liquids through filters as used in reverse osmosis processes. Centrifugation is a technique that helps to separate mixtures by applying centrifugal force. Centrifugation can separate particles from a solution according to their size, shape, density, medium, viscosity, or rotor speed. Screening, or mechanical screening, involves taking granulated or crushed material and separating it into multiple grades by particle size. Milling includes pebble milling, also referred to herein as ball milling, which is a size reduction technique that uses media in a rotating cylindrical chamber to mill materials to a fine powder. (See FIGS. 3A-3B.) As the chamber rotates, the media can lift up on the rising side and then cascade down from near the top of the chamber. Chopping involves cutting the particles to reduce the size and can be accomplished via any chopping tool, such as a knife, axe, or scissors, for example. Sieving is a technique for separating particles of different sizes. It involves separating a particle of interest from unwanted materials with the use of a sieve, which can be a screen such as woven mesh, net, or perforated sheet material, for example.

Chemical separation includes, but is not limited to, chromatography, distillation, evaporation, filtration, crystallization, adsorption, or membrane processes.

Fermentation is a biological process in which sugars or carbohydrates are converted into cellular energy, wherein they can produce ethanol and carbon dioxide as by-products.

The feedstock for fermentation can include sugars and/or carbohydrates, which can include glucose, galacturonic acid, arabinose, galactose, xylose, oligomeric forms of cellulose, pectin xylan, arabinan sugars, bagasse, or any combination thereof.

Bagasse is a solid, non-hydrolyzed plant material. In some embodiments, bagasse does not contain any rubber. In further embodiments, bagasse can include the root skins of the plants used.

Biofuels are liquid fuels and include ethanol and biodiesel. Biofuels can be produced from biomass, wherein biomass can include plant starches, sugars, cellulose, hemicellulose, or any combination thereof. A common method for making biofuel is via fermentation, as discussed above. Bioproducts refer to materials, chemicals, and energy derived from renewable biological resources. Similar to biofuels, this can include plant starches, sugars, cellulose, hemicellulose, or any combination thereof.

Methods

Provided herein is a method of purifying rubber from a plant that naturally produces rubber, the method including: a) contacting plant material with hot water or a dilute basic aqueous solution, thereby forming a plant material composition with a concentration of 3% or less of water extractable materials by weight and an inulin-containing composition; b) separating the plant material composition from the inulin-containing composition; c) pebble milling the plant material composition in the presence of enzymes; d) centrifuging the product of step c) to separate rubber from other material; and e) removing the rubber.

In some embodiments, the plant material composition can have 3% or less, 2% or less, or 1% or less of water extractable materials. In further embodiments, the plant material composition can have from 0% to 1%, 1% to 2%, or 2% to 3% of water extractable materials by weight. In certain embodiments, the plant material composition can have from 0% to 0.5%, 0.5% to 1%, 1% to 1.5%, 1.5% to 2.0%, 2.0% to 2.5%, or 2.5% to 3.0% of water extractable materials by weight.

In some embodiments, the inulin-containing composition can include 90% or more of the total inulin contained in the plant material. In further embodiments, the inulin-containing composition can include 90% or more, 91% or more, 92% or more, 93% or more, 94% or more, 95% or more, 96% or more, 97% or more, 98% or more, 99% or more, or 100% of the total inulin contained in the plant material. In certain embodiments, the inulin containing composition can include from 90% to 91%, 91% to 92%, 92% to 93%, 93% to 94%, 94% to 95%, 95% to 96%, 96% to 97%, 97% to 98%, 98% to 99%, r 99% to 100% of the total inulin contained in the plant material.

As used herein, water extractable materials include, but are not limited to, proteins, fatty acids, inulin, sucrose, terpenes, nucleic acids, carboxylic acids. Further, water extractable materials may include, ash, non-proteinogenic amino acids, crude fat, phenols, water soluble cations, such as potassium, calcium, magnesium, and sodium, water soluble anions, such as $PO_4$, $NH_3$, $SO_4$, F, and Cl, and water soluble sugars, such as nystose, 1-Kestose, glucose, and fructose.

The inulin extracted roots, or plant material, are digested with pectinases, cellulases, hemicellulases, proteases, commercial enzymes, or a group of enzymes produced by MO enriched on TK bagasse (enzymes that dissolve pectin, an interconnected cell wall component in the root, hemicellulose, cellulose a structural carbohydrate). Mechanical forces can increase surface area by reducing particle size and so exposing the cell wall component to the enzymes. This process can liquefy the solid roots and liberate the rubber. As compared to the Eskew process, and previously described enzymatic processes, the total volume of material that is processed after inulin extraction is reduced, due to the fact that the enzymatic digestion step can be done using wet solid roots, without adding additional water to form a slurry.

Further, the enzymatic hydrolysis of cellulose, hemicellulose, pectin and other structural carbohydrates in the root with cellulase, pectinase and hemicellulase enzymes can deconstruct the hemicellulose and cellulose components and pectin sheath of the cell wall of the dandelion root structure to release rubber. Simultaneous pebble milling can facilitate and accelerate this hydrolysis by reducing the particle size of the roots and bagasse to improve enzyme accessibility and can result in rubber quality much greater than that produced by the Eskew process and greater and more efficiently (in less time) than previously described enzymatic processes.

In some embodiments, the plant that naturally produces rubber can include *Parthenium argentatum* (Guayule bush), *Taraxacum kok-saghyz* (Russian dandelion), *Taraxacum brevicorniculatum, Taraxacum officianales, Euphorbia lathyris* (plant gopher), *Parthenium incanum* (mariola), *Chrysothamnus nauseosus* (rabbit brush), *Pedilanthus macrocarpus* (candililla); *Asclepias syriaca, speciosa, subulata*, (milkweed), *Solidago altissima, graminifolia rigida*, (goldenrod), *Cacalia atripilicifolia* (pale Indian banana), *Pycnanthemum incanum* (mountain mint), *Teucrium canadense* (American camedrio), *Campanula americana*, or any combination thereof. In further embodiments, the plant that naturally produces rubber can include *Taraxacum kok-saghyz* (Russian dandelion). One of skill in the art can readily identify other species of plants comprising rubber that can be used with the methods disclosed herein.

In certain embodiments, the pebble milling and addition of enzymes in step b) can occur simultaneously. By "simultaneously" is meant substantially at the same time, or concurrently. Conversely, the pebble milling and addition of enzymes can happen sequentially, so that one follows the other. In further embodiments, the processes overlap so that at least a part of both processes happen at the same time, but not the entire process.

In some embodiments, no additional water is used during step b). Other substances, such as other liquids (like buffers) and enzymes may be used, or there can be no addition of any other material during pebble milling.

In specific embodiments, centrifugation can be at 1 g or greater. In some embodiments, centrifugation can be at 500 g or greater, 2000 g or greater, 10000 g or greater, 15000 g or greater, 20000 or greater, or 25000 g or greater. In further embodiments, centrifugation can be from 1 g to 1000 g, 1000 g to 2500 g, 2500 g to 5000 g, 5000 g to 7500 g, 7500 g to 10000 g, 10000 g to 12500 g, 12500 g to 15000 g, 15000 g to 17500 g, 17500 g to 20000 g, 20000 g to 22500 g, or 22500 to 25000 g. In certain embodiments, centrifugation can be from 20000 g to 21000 g, 21000 g to 22000 g, 22000 g to 23000 g, 23000 g to 24000 g, or 24000 g to 25000 g. In specific embodiments, centrifugation can be from 23000 g to 23200 g, 23200 g to 23400 g, 23400 g to 23600 g, 23600 g to 23800 g, 23800 g to 24000 g, 24000 g to 24200 g, 24200 g to 24400 g, 24400 g to 24600 g, 24600 g to 24800 g, or 24800 g to 25000 g. The mixture can be centrifuged for 5, 10, 15, 20, 25, 30, 35, 40, 45, 50, 55, or 60 minutes, or any amount below, above, or in-between these amounts.

In some embodiments, centrifugation can result in at least three separate fractions, wherein the three separate fractions can include an upper fraction, a middle fraction, and a lower fraction. In further embodiments, the upper fraction can include 95% or more of the rubber from the plant. In some embodiments, the upper fraction can include 95% or more, 96% or more, 97% or more, 98% or more, 99% or more, or 100% of the rubber from the plant. In further embodiments, the upper fraction can include from 95% to 96%, 96% to 97%, 97% to 98%, 98% to 99%, or 99% to 100% of the rubber from the plant. In some embodiments, the upper fraction can comprise substantially "pure" rubber and can have 10% or less of other non-rubber materials. In further embodiments, the rubber can be from 90% to 100% pure. In certain embodiments, the rubber can be from 90% to 91%, 91% to 92%, 92% to 93%, 93% to 94%, 94% to 95%, 95% to 96%, 96% to 97%, 97% to 98%, 98% to 99%, or 99% to 100% pure. In specific embodiments, the rubber can be 90% or more, 91% or more, 92% or more, 93% or more, 94% or more, 95% or more, 96% or more, 97% or more, 98% or more, 99% or more, or 100% pure.

In certain embodiments, the middle fraction can include enzymes, monomeric sugars, oligomeric sugars, or any combination thereof. In further embodiments, the middle layer can include water soluble components remaining after centrifugation. In some embodiments, the middle fraction can be a clear liquid. In further embodiments, the enzymes and saccharides are a result of enzymatic Hydrolysis. The middle fraction, and the enzymes it contains, can be recycled, and sugars can be separated for fermentation and to avoid inhibition of enzymatic activity.

In specific embodiments, the lower fraction can include bagasse. In certain embodiments, the lower fraction is a higher density solid bagasse fraction and includes no rubber.

In further embodiments, the upper fraction of rubber can be separated. In some embodiments, the upper fraction of rubber can be separated from the middle fraction and lower fraction by scooping it from the other fractions. In certain embodiments, the method can further include washing the upper fraction of rubber. In specific embodiments, the method can further include further separating water and other liquids from the upper fraction of rubber.

In some embodiments, further separating the upper fraction of rubber can include mechanical separation. In further embodiments, mechanical separation can include screening, pebble milling, or any combination thereof. These mechanical separation methods remove small amounts of residual non-rubber material. Those of skill in the art will understand how to carry out a secondary step of mechanical separation. A novel aspect of the present disclosure includes the fact that final mechanical separation of rubber from residual root material can be performed by either secondary milling or screening and hydraulic washing or both.

Screening involves separating solid particles according to size. It can involve taking granulated or crushed material and separating it into multiple grades by particle size. It can be performed as dry screening or wet screening, and particles can be categorized into a moving screen or static screen and the screen can be either horizontal or on an incline. In some embodiments, the screening machine includes a drive that induces a vibration, either sinusoidal or gyratory, and a screen media that causes particle separation. The rate or cut of screening can be determined based on vibration, g force, bed density or material shape. In further embodiments, screening uses gravity, density, and/or electrostatic force when separating particles. Types of screening equipment include a tumbler screener, circle-throw vibrating equipment, high frequency vibrating equipment, gyratory equipment, and/or trommel screens. Screen media used in screening can include woven wire cloth, perforated and punch plate, synthetic screen media, or self-cleaning screen media.

Hydraulic washing is a type of gravity separation wherein particles are passed through an upward stream of water causing the lighter particles to be separated from the heavier particles.

In certain embodiments, further separating the upper fraction of rubber can include chemical separation.

In specific embodiments, products other than rubber can be extracted and purified.

In further embodiments, one or more of the products can be used as feedstock for fermentation. Fermentation has a definition as described herein.

In certain embodiments, one or more of the products can be used for the production of biofuel. Biofuel has a definition as described herein.

In specific embodiments, one or more of the products can be used for the production of bioproducts. Bioproducts has a definition as described herein.

In some embodiments, the method can be completed in less than 6 hours. In some embodiments, the method can be completed in less than 5 hours, less than 4 hours, less than 3 hours, less than 2 hours, or less than 1 hour. In further embodiments, the method can be completed in from 0 hours to 1 hour, 1 hour to 2 hours, 2 hours to 3 hours, 3 hours to 4 hours, 4 hours to 5 hours, or 5 hours to 6 hours.

The method described herein generates rubber with less than 1% "dirt" (meaning non-rubber material) as measured by ASTM D1278. For example, there can be less than 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29; 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, or 0.99% dirt in the final rubber product. (See FIG. 11.)

The method described herein can yield more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the rubber present in the roots. In a preferred embodiment, the method yields more than 80% of the rubber present in the roots. The rubber can meet technical grades 10 and 20 as described in ASTM 2227. Water extracted roots can be amended with antioxidants to prevent rubber oxidation and degradation during subsequent process steps such as pretreatment with acid/base/ionic liquids.

In some embodiments, the method can further comprise contacting the plant material with an antioxidant. In further embodiments, the antioxidant can include primary antioxidants. In certain embodiments, primary antioxidants can include phenolic antioxidants, amine antioxidants, or any combination thereof. In further embodiments, the antioxidant can include secondary antioxidants. In certain embodiments, the secondary antioxidants can include phosphite antioxidants, thioester antioxidants, or any combination thereof. Antioxidants can be used in the rubber industry to prevent rubber degradation during rubber production, storage, and/or processing. Antioxidants can be highly effective ingredients having a dramatic impact on the service life of a rubber product despite being present at low concentrations. Antioxidants can inhibit the rate of auto oxidation by interfering with radical propagation reaction. Primary antioxidants are chain terminating antioxidants, secondary antioxidants are peroxide decomposers. Chain terminating antioxidants can scavenge free radicals before they have an opportunity to rapidly grow in numbers and peroxide decomposers reduce the peroxides and hydroperoxides to alcohols before they produce additional radicals.

Roots can also be treated with TK enriched MO and their enzymes (including ligninolytic enzymes). The novel aspects of the PENRA V process include the fact that no water addition is needed. Enzymes and buffer alone can be added to the roots and can result in more concentrated enzyme solution, reduced volume, and less liquid to separate in subsequent steps.

Composition

Also provided herein is a product that can be obtained by any of the processes disclosed herein.

In some embodiments, the products can include monomeric sugars. In further embodiments, monomeric sugars can include glucose, galacturonic acid, arabinose, galactose, xylose, or any combination thereof. In certain embodiments, the products can include oligomeric sugars. In some embodiments, the oligomeric sugars can include combinations of monomeric sugars. In specific embodiments, the oligomeric sugars can include oligomeric forms of cellulose, hemicellulose, pectin, or any combination thereof. In some embodiments, the oligomeric sugars can include cellobiose.

In some embodiments, the product can include rubber, wherein rubber is defined as disclosed herein.

In further embodiments, the rubber can include no more than 1% dirt after step c). As used herein, "dirt" is measured by ASTM D1278. In some embodiments, the rubber can meet the technical grades 10 and 20 as described in ASTM 2227. In some embodiments, the rubber can include no more than 0.8%, 0.6%, 0.4%, 0.2% or 0% dirt after step c). In further embodiments, the rubber can include from 0% to 0.25%, 0.25% to 0.5%, 0.5% to 0.75%, or 0.75% to 1.0% dirt after step c). In certain embodiments, the rubber can include from 0% to 0.1%, 0.1% to 0.2%, 0.2% to 0.3%, 0.3% to 0.4%, 0.4% to 0.5%, 0.5% to 0.6%, 0.6% to 0.7%, 0.7% to 0.8%, 0.8% to 0.9%, or 0.9% to 1.0% dirt after step c). (See FIG. 11.)

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. There are numerous variations and combinations of process conditions that can be used to optimize product quality and performance. Only reasonable and routine experimentation will be required to optimize such process conditions.

Example 1: Rubber Extraction Process Methods

Materials and Methods

Figure 4A:
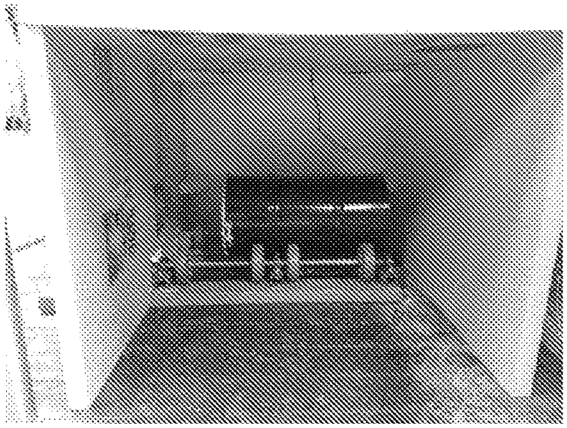
FIGS. 4A-4B show (FIG. 4A) a barrel roller with a 10 gallon barrel with a space heater used for heating, and (FIG. 4B) an insulated box with 4-inch Styrofoam and a feedback temperature controller set to 45-50° C.
Figure 4B:
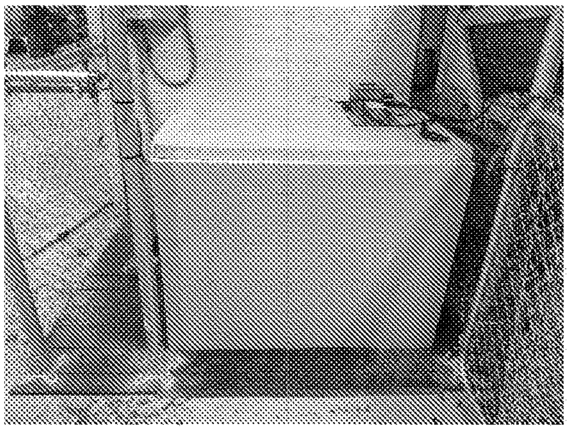

Method included a 10 gallon barrel used on a barrel roller with small amount of grinding media (usually less than 2 liters of grinding media is used), 4.05 kg water extracted roots (dry weight basis) per run (n=3) (see FIGS. 3-4), inulin extracted using hot water and the remaining solids drained, solids pretreated with 1.4 g NaOH, 1.4 g $H_2SO_4$ at 121° C. or not pretreated, added to barrel with: 1 liter 0.1M pH 5.0 citrate buffer, 250 ml pectinase enzyme (XPE), 350 ml cellulase enzyme (XCE 150, 2018), and 12.5% g enzyme/g roots. The materials underwent a 3 h reaction time at 50 RPM at 50° C.

CONCLUSIONS

Alkaline pretreatment increased yield, but the rubber degraded. The removal of phenolic compounds hastened oxidation. Antioxidant addition prior to pretreatment improved this. Microorganisms enriched on TK roots improved rubber yield and purity when used as a pretreatment. Pretreatment enhanced the effects of rubber aging.

Enzyme dose and hydrolysis time were reduced substantially compared to previous methods without affecting yield and purity in the PENRA V process, thereby reducing capital and operating costs for a commercial process. Cellic CTec 2 resulted in higher yields and purities than Accellerase 1500 or CT cellulases used previously. (See FIGS. 7-11.)

The following antioxidants were evaluated during pretreatments: Pentaerythritol tetrakis(3,5-di-tert-butyl-4-hydroxyhydrocinnamate, Octadecyl 3-(3,5-di-tert-butyl-4-hydroxyphenyl) propionate, and (+)-α-Tocopherol (more environmentally-friendly option).

Microbial communities were enriched with TK root bagasse for pretreatment. Milling conditions, including RPM, media, roots to liquid ratio, were optimized. Enzyme reuse was evaluated and cellic CTec 2 was obtained for pilot scale testing. Additionally, TK Inulin purification and characterization were revisited.

Example 2: Effects of Alkaline Pretreatment Temperature and Concentration

The alkaline conditions were 33, 66, and 132 mg NaOH/g dry biomass. The temperatures were 25° C., 70° C., 120° C., and 160° C. for 20 min.

Enzyme digestion included 1 L Erlenmeyer flask of 300 ml volume, 6% solids (60 mg of water extracted roots (dry weight basis) per mL), 0.5 mol L"1 sodium citrate buffer (pH 5.5), cellic CTec2 and pectinase at a ratio of 1.75:1 at 16 mg protein/g dry roots, and incubating at 50° C., 180 rpm, for 48 h in a shaker incubator. (See FIGS. 9-11).

Example 3: Biological Pretreatment+PENRA V Process-Rubber Yield and Purity

Figure 20:
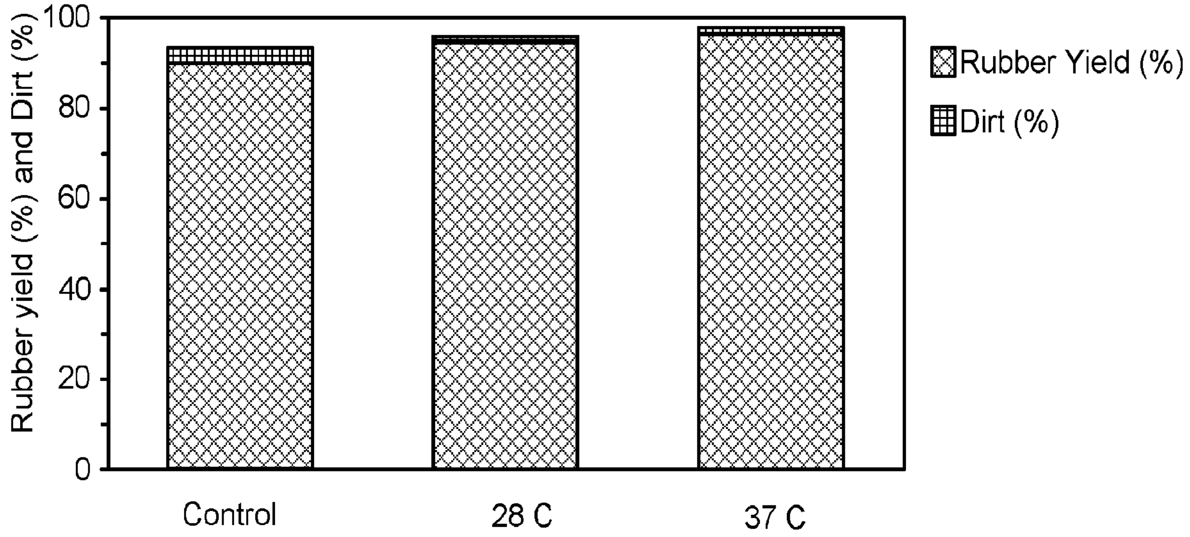
FIG. 20 shows the rubber yield (%) and purity (%) at a control temperature, 28° C., and 37° C. for rubber that has undergone biological pretreatment and PENRA processing.

Inoculum was prepared by inoculating water extracted roots with compost and water. It was then shaken and incubated at 28° C. and 37° C. After 15 days, the roots were removed. Cultures were used to inoculate about 315 g of water-extracted roots (approximately 28 g dry weight). Roots were incubated at 150 rpm at both 28° C. and 37° C. for one week. Pretreated roots were transferred to a 2 L jar. Rubber was then extracted using enzymatic hydrolysis for 48 h at 50° C. (See FIG. 20).

Example 4: Alkaline Pretreatment of *Taraxacum kok-saghyz* (TK) Roots for the Extraction of Natural Rubber (NR)

INTRODUCTION

Alkaline pretreatment significantly improved the yield of TK NR using this method, but its effects on NR yield, purity, and quality at a range of base concentrations and temperatures was not tested. In this study, TK roots (after inulin extraction) were pretreated at sodium hydroxide loading rates of 0, 33, 66 and 132 mg NaOH/g and temperatures of 25, 70, 125 and 160° C. Treatment with pectinase and cellulase enzymes was used to solubilize root structural carbohydrates and liberate NR. Rubber quality and impurities were then characterized. Results showed that increasing NaOH loading rate and temperature significantly improved rubber yield, but reduced rubber molecular weight and rubber gel content. Rubber purity and thermal properties were largely unaffected by pretreatment conditions. FTIR and SEM analysis revealed that alkaline pretreatment primarily altered protein and other secondary components of TK NR.

The molecular weight of natural rubber was widely used to assess the quality of NR since it was directly related to rubber processability and mechanical properties (Johnson, 1948; Gao et al., 2015; Gentekos et al., 2019; Westall, 1968; Subramaniam, 1972). Here, the effects of alkaline pretreatment at a range of NaOH loading rates and reaction temperatures on the yield, purity, and quality of TK natural rubber were investigated. Roots were initially extracted with hot water to remove inulin, and then pretreated with NaOH under various conditions. Pretreated roots were then digested using cellulases, hemicellulases, and pectinases to separate the NR from other root components. Rubber purity and quality were assessed by measuring the rubber impurity content, and molecular weight and molecular size distribution, respectively. The effects of alkaline pretreatment were also investigated using Fourier-transformed infrared spectroscopy (FTIR), differential scanning calorimetry (DSC), thermo-gravimetric analysis (TGA), gel content measurement and scanning electron microscopy (SEM) to determine its impact on rubber components.

Materials and Methods 1.1. Chemical Reagents, Enzymes, and Rubber

Chemicals used during this study were purchased as reagent grade or equivalent.

Cellulase (Cellic® CTec2) and pectinase (NS-81215) were donated by Novozymes (Novozymes, Franklinton, NC). Hevea standard Vietnamese rubber grade L (SVRL) was purchased from Centrotrade (Chesapeake, VA, USA).

1.2. TK Roots

TK roots were obtained from the Oregon State University-Southern Oregon Research and Extension, Central Point, OR. Four seed populations obtained from the Ohio State University were planted in the autumn of 2014 at an average density of 48 plants per $m^2$. Plants were harvested in the autumn of 2015 and washed with water to remove soil. Rosettes were cut above the crown and removed. The roots were dried at 50° C. for 4-7 days. Dried roots were stored in a tote and shipped to Wooster, Ohio.

The dry TK roots were roller-cut and flattened as described previously (Ramirez-Cadavid et al., 2019). The cut roots were thoroughly mixed and six sub-samples of approximately 1 kg each from different parts of the tote were taken and stored in sealed bags at 4° C. The moisture content, ash, water extractables, acetone extractables (resins), and hexane extractables (rubber), were measured using methods described previously (Ramirez-Cadavid et al., 2018). The dried roots had a moisture content of 6.4±0.3% (w/w) and an ash content of 10.4±0.1%. They contained 60.6±0.9% water extractables (inulin and proteins), 1.5±0.0% acetone extractables (resins), and 5.2±0.4% hexane extractables (natural rubber).

1.3. TK Root Processing 1.3.1. Inulin Extraction

Eight-hundred grams of the cut TK roots were extracted six times with deionized (DI) water at 98-100° C. for 20 min and drained as previously described (Ramirez-Cadavid et al., 2019). Moisture content was determined gravimetrically after drying five subsamples of water extracted roots (approximately 20 g wet weight) at 105° C. for 24-36 h (Ramirez-Cadavid et al., 2019). The remaining water extracted roots were separated into 14 parts of about 340 g wet weight each (27 g dry weight). These were stored at 4° C. (for at most 3 days).

1.3.2. Alkaline Pretreatment and Enzymatic Digestion

The 340 g subsamples of water extracted roots were pretreated with NaOH at concentrations of 0, 33, 66, and 132 mg NaOH/g dry biomass. The pretreatments were conducted at a solid loading rate of 6.0% (60 mg of dried water extracted roots per mL) in a volume of 0.5 L. Duplicate treatments of 25° C., 70° C., 120° C., and 160° C. for 20 min were conducted in 1 L containers. The lower temperature treatments (25° C. and 70° C.) were incubated in an Innova 4230 and Innova 3100 shaker (New Brunswick Scientific, Edison, NJ), respectively. The temperature inside the flasks was monitored by a thermocouple. An autoclave was used for pretreatments at 120° C., 0.103 MPa for 20 min (Amsco® Lab 250, Steris Corporation, Mentor, OH). Pretreatments at 160° C. with 0.483 MPa were performed in a 1 L high-pressure/high-temperature 316 stainless steel Parr reactor (Ramirez-Cadavid et al., 2019).

The pretreated material was filtered (297 μm filter, sieve No. 50) and washed with 12 L DI water. The solid fraction was suspended in 1.8 L of DI water and stored at 4° C. overnight to remove residual alkalinity from the biomass. The solids were then filtered again through a 297 μm filter (sieve No. 50) and transferred to 1 L Erlenmeyer flasks, and the pH of the liquid fraction was measured and found to be between 5 and 6. CTec2 and pectinase were added at a concentration of 16 mg protein/g dry roots, and in a loading ratio of 1.75:1 Ctec2 to pectinase, which corresponded to doses of 52 and 27.5 μL/g dry roots, respectively. Lastly, sodium azide (0.7% w/v final concentration) and 0.5 mol $L^{-1}$ citrate buffer (pH 5.5) were added to inhibit microbial growth. The flasks were sealed and incubated at 50° C., 180 rpm, for 48 h in an Innova 4300 shaker incubator (New Brunswick Scientific, Edison, NJ). Protein concentration of CTec2 was measured using a protein assay kit (Pierce™ Modified Lowry Protein Assay Kit, Thermo Scientific, Waltham, MA, USA).

Control treatments consisted of the unpretreated roots digested using CTec2 and pectinase enzymes, sodium citrate buffer, and sodium azide as described above.

After enzymatic digestion, the slurry was centrifuged at 4150 rpm for 15 min (Sorvall T Plus centrifuge, swinging bucket rotor 75006445, ThermoFisher Scientific, Waltham, MA). This resulted in three fractions: solid rubber (top layer), liquid in the middle, and bagasse material on the bottom. The rubber was removed, and pebble milled as described previously (Stolze et al., 2017). The filled material was placed into a 7 L container, DI water was added, and rubber was collected and weighed.

1.3.3. Rubber Drying

Wet rubber was cut into small pieces of about 0.5 cm using scissors, dried at 50° C. for 24 h and stored at −20° C. This material was defined as "crude TK natural rubber".

1.4. Characterization of TK Natural Rubber 1.4.1. Dirt (Impurity) Content

Dirt content of crude TK natural rubber was measured according to ASTM D1278-91 (Ramirez-Cadavid et al., 2019; American Society for Testing and Materials, 2015). The crude rubber was dissolved in turpentine and filtered, and the dried solid fraction retained on a 45 μm sieve was called "dirt" while the dissolved material was termed, "purified rubber" (Stolze et al., 2017). Dirt consisted mostly of lignocellulosic material.

1.4.2. Rubber Yield

Rubber yield was defined as the amount of purified rubber recovered divided by the total solids recovered using hexane and acetone extraction by accelerated solvent extraction.

$$\text{Rubber yield}\left(\%\frac{w\text{ rubber}}{w\text{ theoretical rubber}}\right)=\left(\frac{\text{purified rubber}\left(\%\frac{w\text{ rubber}}{w\text{ dried }TK\text{ root}}\right)}{\text{acetone fraction}\left(\%\frac{w\text{ acetone extractables}}{w\text{ dried }TK\text{ root}}\right)+\text{hexane fraction}\left(\%\frac{w\text{ hexane extractables}}{w\text{ dried }TK\text{ roots}}\right)}\right)\times 100$$

1.4.3. Rubber Gel Content

Gel content of crude rubber samples was determined in accordance with ISO/DIS 17278:2012 (ISO/DS 17278). The toluene insoluble fraction contained both the dirt fraction and the rubber gel. Therefore, the amount of rubber gel was calculated by subtracting the dirt content from the toluene insoluble content.

1.4.4. Gel Permeation Chromatography (GPC)

Figure 5A:
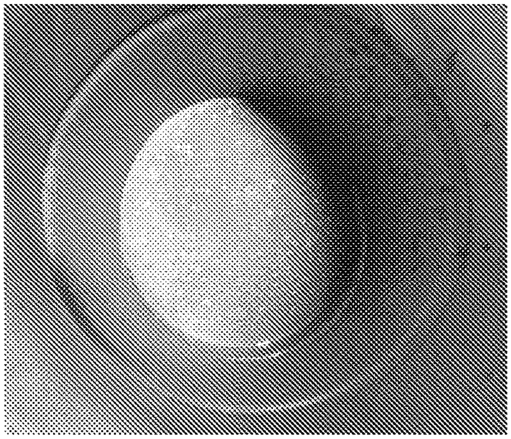
FIGS. 5A-5B show (FIG. 5A) liquefied roots after 48 hours digestion and (FIG. 5B) the rubber recovered after first flotation.
Figure 5B:
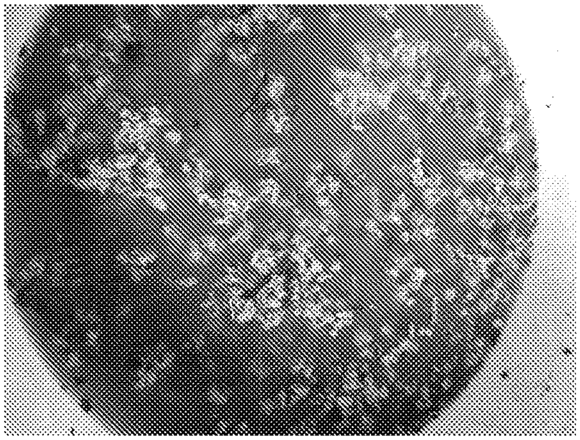
Figure 6A:
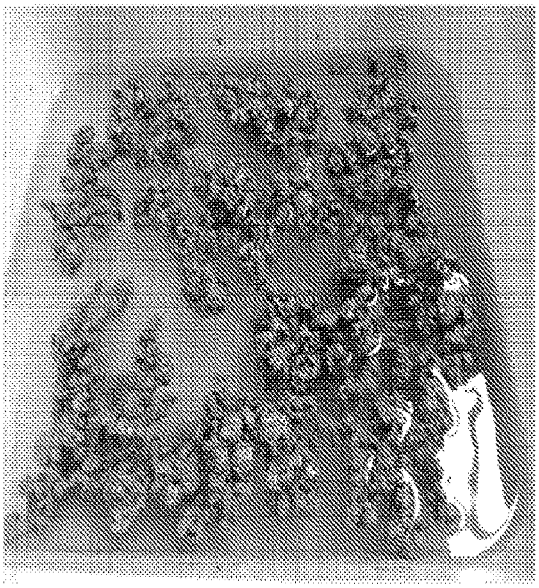
FIGS. 6A-6B show (FIG. 6A) rubber after pebble milling and (FIG. 6B) the second flotation and the recovered rubber, which was the cleanest to date at PENRA pilot scale when documented.
Figure 6B:
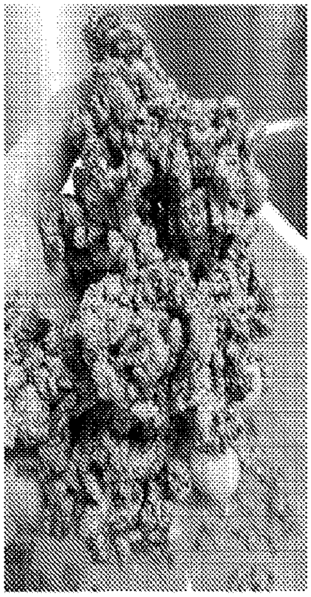
Figure 7A:
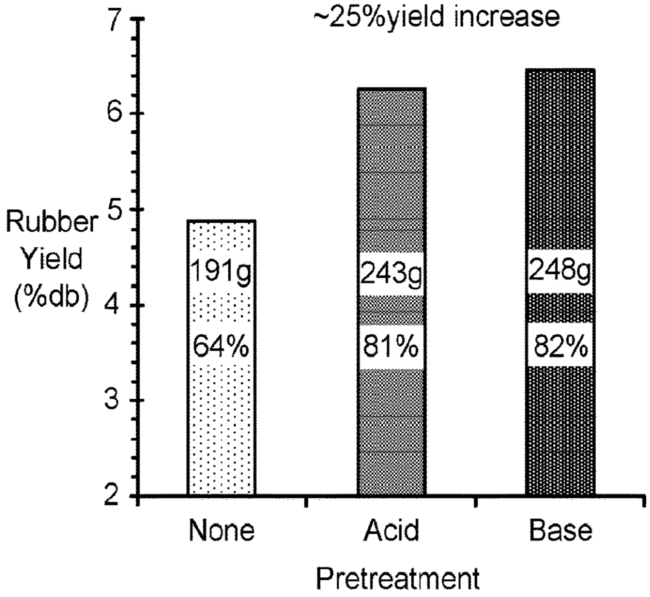
FIGS. 7A-7B show the effects of pretreatment for pilot scale PENRA V. More specifically.
Figure 7B:
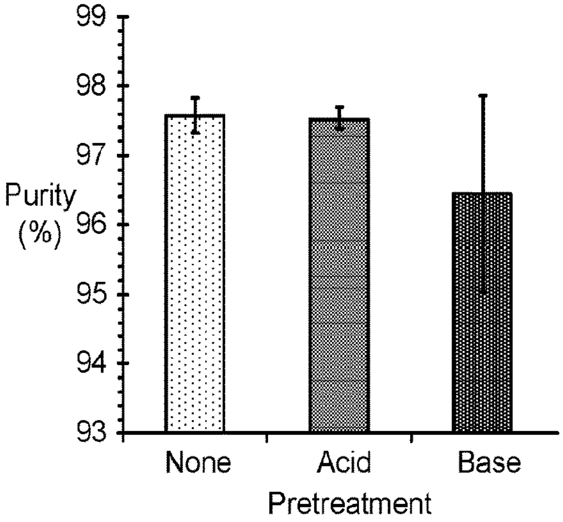
Figure 8:
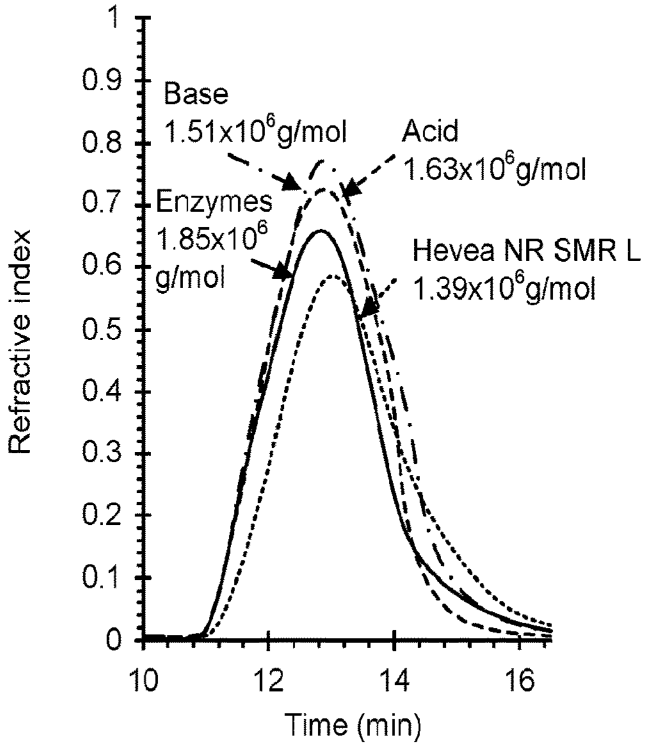
FIG. 8 shows molecular weight as demonstrated by gel permeation chromatography.
Figure 9:
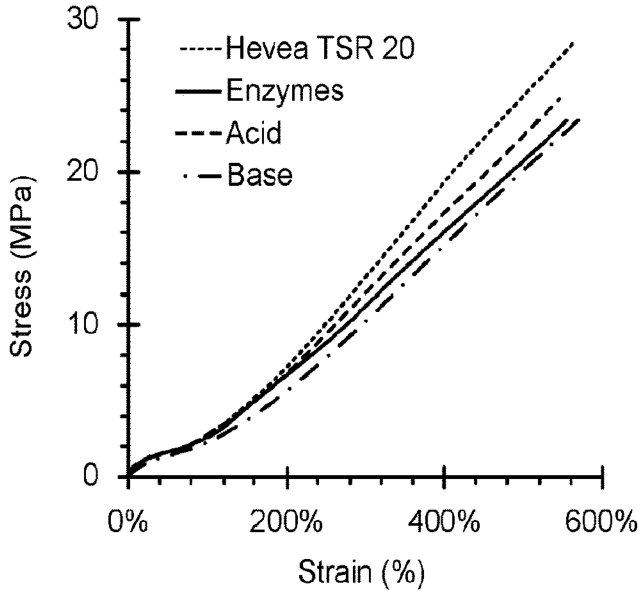
FIG. 9 shows tensile strength data for compounded Hevea TSR 20, enzymes, acid, and base.
Figure 14:
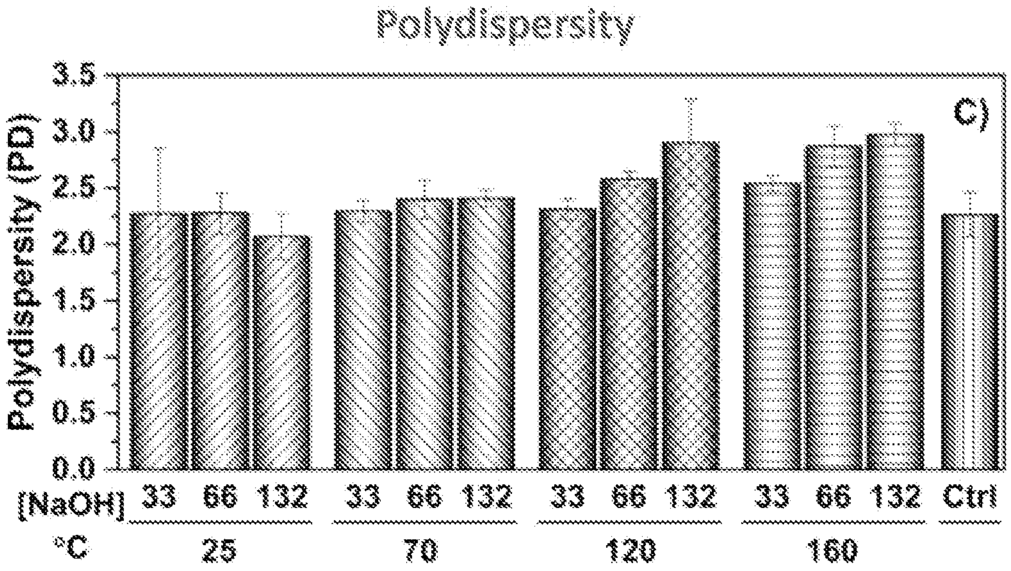
FIG. 14 shows the polydispersity ($M_W/M_N$) of exemplary rubber pretreated at 25° C., 70° C., 120° C., and 160° C., with NaOH concentrations of 0, 33 mg NaOH/g dry roots, 66 mg NaOH/g dry roots, and 132 mg NaOH/g dry roots.

The molecular weight distribution of crude TK NR from each treatment was determined using gel permeation chromatography (GPC) following a procedure previously described (Ramirez-Cadavid et al., 2019). (See FIGS. 5A-5B.)

1.4.5. Thermogravimetric Analysis (TGA)

Samples (10 mg) of crude rubber from each treatment were analyzed by TGA under nitrogen using a TA Q50: thermogravimetric analyzer (TA Instruments, New Castle, DE) as described previously (Ramirez-Cadavid et al., 2019). The raw data were analyzed using TRIOS software (TA instruments). Thermal events in crude rubber were identified as: sample moisture loss at 100° C.; degradation onset temperature (Onset T or initial decomposition temperature); weight loss at Onset T; D1/2 which is defined as the temperature at which 50% of the sample weight has been lost; maximum rate of decomposition temperature (MRDT), which is associated with the temperature at which the primary component of the sample de-composes; and final residue (FR), which is the residual material, or ash, left after the crude TK NR has been heated to 575° C. under TGA conditions.

1.4.6. Differential Scanning Calorimetry (DSC)

An 8 mg sample of crude rubber from each treatment was analyzed by DSC using a TA Q20 differential scanning calorimeter (TA Instruments, New Castle, DE) as described previously (Ramirez-Cadavid et al., 2019) and the data were analyzed using TRIOS software (TA instruments), to determine the glass transition temperature ($T_g$).

1.4.7. Fourier Transform Infrared Spectroscopy

A sample (15-20 mg) of dried TK NR from each treatment was analyzed by FTIR. FTIR spectra were recorded using a Spectrum Two™ instrument (Perkin Elmer Inc., Waltham, MA) equipped with a universal attenuated total reflectance accessory (UATR). The methodology used to obtain the spectra and the data analysis including second derivative of FTIR spectra is as described previously (Ramirez-Cadavid et al., 2019).

1.4.8. Scanning Electron Microcopy (SEM)

For SEM analysis, samples of crude TK NR, and dirt recovered from rubber samples, were dried in a semiautomatic critical point drying apparatus (Samdri-790, Tousimis, Rockville, MD). The dried samples were stub mounted with carbon conductive tape and platinum sputter coated. The samples were visualized using a Hitachi S-3500 N scanning electron microscope.

1.5. Severity Factor ($M_0$)

The severity of the alkaline pretreatment ($M_0$) of TK roots was calculated using time, temperature, and alkaline loading rate based on the equation below, and used to correlate the pretreatment severity with rubber yield. The severity factor was first developed for steam explosion pretreatment of biomass (Overend et al., 1987), and later for acid (Chum et al., 1990) and alkaline (Silverstein et al., 2007) pretreatment of biomass. The factor for alkaline pretreatment can be calculated based on the following equation:

$$M_0 = tC^n\exp\left(\frac{T-100}{14.75}\right)$$

Where $M_0$ is the severity factor; t is reaction time (min); C is the NaOH loading (% w/w); T is the reaction temperature (° C.); n is a constant fitted for NaOH equals to 3.90 (Silverstein et al., 2007). (See FIG. 21.):

1.6. Statistical Analysis

A full factorial experimental design was used with temperature at four levels and NaOH loading at three. Factorial effect models with main effects and interaction effects on rubber yield, dirt content, and molecular mass were fit using JMP® Pro 14 software. Multiple comparisons among treatment means were carried out using the Tukey HSD statistical procedure. Significant interactions were evaluated using Test Slices. The significance level (α) was set at 0.05.

2. Results 2.1. Rubber Yield, Dirt Content, and Rubber Gel

Sodium hydroxide loading and reaction temperature both significantly increased rubber yield (p-value<0.05). The mean rubber yields in alkaline pretreated treatments, at the highest and the lowest temperatures, were 78.2% and 70.0% w/w % w/w, respectively, which were 22.6% and 9.7% greater than the unpretreated control (63.8% w/w). Rubber yields at the highest and the lowest NaOH loadings were 77.2% and 70.1% w/w, respectively, 21.0% and 9.9% greater than the control (63.8% w/w). Increasing the reaction temperature from 25° C. (lowest) to 160° C. (highest) increased yield by 12% while increasing the sodium hydroxide loading from 33 mg NaOH/g TK roots (lowest) to 132 mg NaOH/g TK roots (highest), significantly increased rubber yield by 10% (Table 1).

TABLE 1

Rubber yield and rubber dirt content as a function of reaction temperature and NaOH loading.

| Temperature °C | NaOH mg/g dry roots | Rubber yield % (w/w) | Dirt % (w/w) |
|---|---|---|---|
| 25 | 33 | 67.65 ± 2.39 | 2.55 ± 0.07 |
| 25 | 66 | 72.18 ± 0.12 | 2.64 ± 0.28 |
| 25 | 132 | 70.09 ± 0.56 | 2.36 ± 0.44 |
| 70 | 33 | 69.07 ± 1.03 | 2.59 ± 0.48 |

TABLE 1-continued

Rubber yield and rubber dirt content as a function of reaction temperature and NaOH loading.

| Temperature °C | NaOH mg/g dry roots | Rubber yield % (w/w) | Dirt % (w/w) |
|---|---|---|---|
| 70 | 66 | 70.61 ± 0.06 | 2.67 ± 0.26 |
| 70 | 132 | 74.84 ± 1.07 | 3.14 ± 0.19 |
| 120 | 33 | 70.29 ± 2.82 | 2.54 ± 0.22 |
| 120 | 66 | 77.27 ± 0.60 | 2.86 ± 0.14 |
| 120 | 132 | 81.18 ± 1.25 | 3.06 ± 0.46 |
| 160 | 33 | 73.29 ± 1.43 | 2.06 ± 0.08 |
| 160 | 66 | 78.76 ± 0.79 | 2.39 ± 0.35 |
| 160 | 132 | 82.60 ± 0.16 | 2.64 ± 0.06 |
| Control | | 62.96 ± 3.75 | 3.14 ± 0.45 |

Control treatment was conducted using non-pretreated roots.
Each value is the mean of 2 + standard deviation.

The interaction of NaOH loading, and reaction temperature also had a significant effect on rubber yield (p-value<0.05) (Table 1). The treatments can be divided into three groups: treatments yielding more than 77% w/w, those yielding between 70% w/w and 75% w/w, and those yielding less than 69% w/w. The treatments in the first group were those with the highest temperatures and NaOH loadings of 160° C. and 120° C., and 132 and 66 mg NaOH/g TK roots, respectively. The highest and the lowest yields in this first group of 82.6% and 77.3% w/w, were produced by 160° C. and 132 mg NaOH/g TK roots, and 120° C. and 66 mg NaOH/g TK roots, respectively. The second yield group contained most of the treatments. The highest and the lowest yields in this group, 74.8% and 70.1% w/w, were obtained by 70° C. and 132 mg NaOH/g TK roots, and 25° C. and 132 mg NaOH/g TK roots, respectively. The third group included the treatments with the yields of 69.1%, 67.6%, and 63.0% w/w that were produced by the 70° C. and 33 mg NaOH/g TK roots treatment, the 25° C. and 33 mg NaOH/g TK roots treatment, and the control, respectively. Rubber yield at the highest and lowest pretreatment severities of 160° C. and 132 mg NaOH/g TK roots, and 25° C. and 33 mg NaOH/g TK roots, was 35% and 6% greater than the control, respectively.

NaOH loading and reaction temperature did not affect dirt content in the crude rubber individually or interactively as a function of temperature or alkaline loading rate. The pooled mean of the dirt contents among treatments was lower at 2.6:0.4% w/w, but not significantly different that the dirt content in the control treatment of 3.1±0.2% w/w (Table 1).

Figure 21:
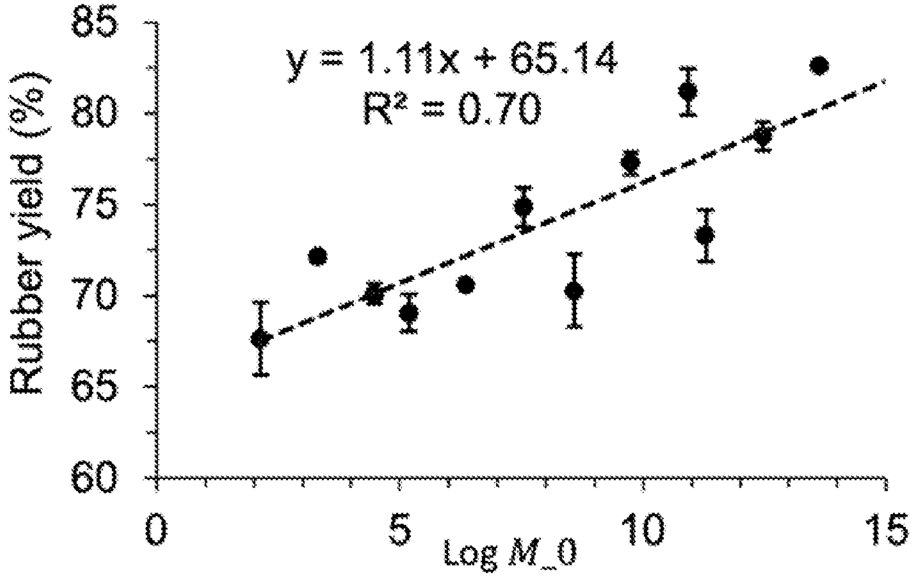
FIG. 21 shows the rubber yield (%) vs. severity factor (Log M0) for different sodium alkaline pretreatments.

Severity factors were calculated for each of the alkaline pretreatment conditions evaluated during this study. Rubber yield was presented as a function of the severity factor (Log M0) (FIG. 21). Rubber yield tended to increase linearly with severity ($R^2$=0.70).

In general, the content of gel in the crude rubber decreased as a function of the reaction temperature. Gel content was 5.1% w/w at the lowest (25° C.), and 4.3% w/w at the highest reaction temperature (160° C.). Gel contents at 70° C. and 120° C. were 4.9% and 4.7% w/w, respectively. The gel content also decreased with NaOH loading rate, but not significantly. Gel contents were 5.8%, 4.6%, 4.8%, and 4.7% w/w at NaOH loadings of 0, 33, 66, and 132 mg NaOH/g TK roots.

2.2. Molecular Weight and Distribution Characteristics

Figure 22:
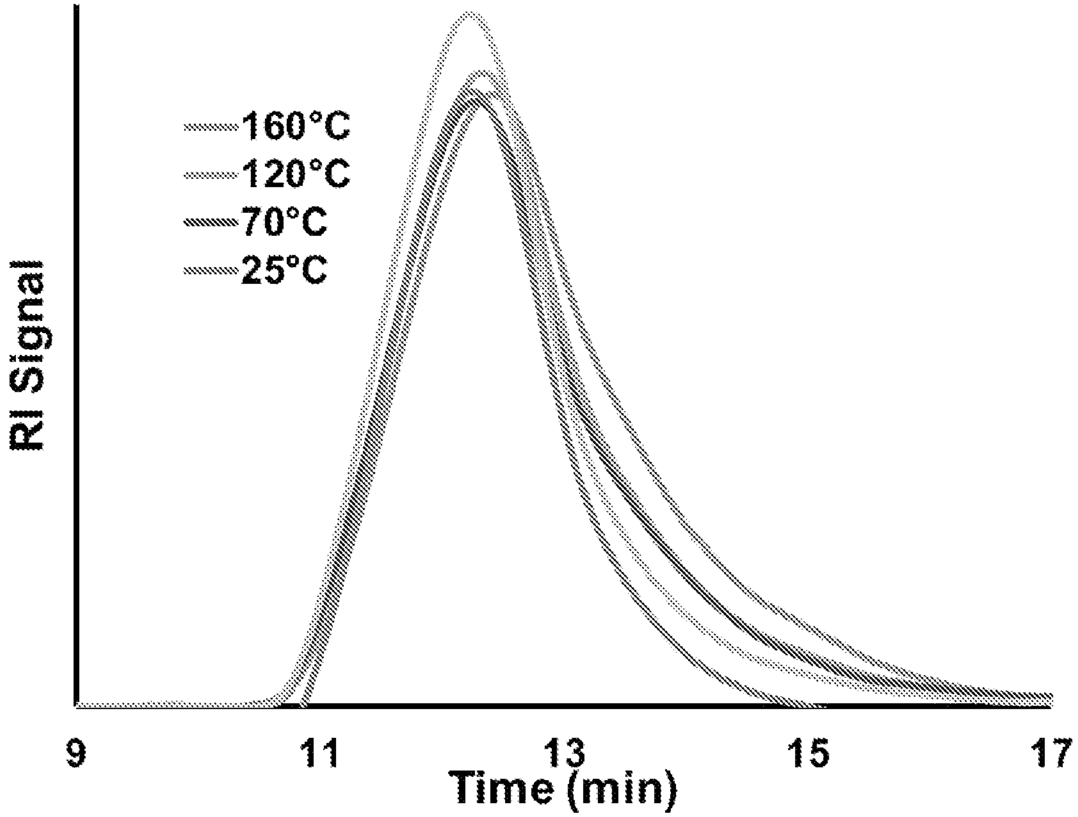
FIG. 22 shows GPC-RI analysis of TK NR obtained by control treatment and alkaline pretreatments at 25° C., 70° C., 120° C. and 160° C., and a sodium hydroxide loading of 66 mg NaOH/g TK. Control treatment was conducted using non-alkaline pretreated roots.

Increasing reaction temperature caused a significant reduction in the rubber number average molecular weight ($M_n$), and weight average molecular weight ($M_w$) and a significant increase in rubber Polydispersity (PD=$M_w/M_n$) (p-value<0.05) (Table 2 and FIG. 22). Comparing treatments at the lowest temperature (25° C.) to those at the highest temperature (160° C.), $M_n$ and $M_w$ were reduced from 0.7 to 0.4×$10^6$ g/mol, and from 1.5 to 1.1×$10^6$ g/mol, respectively, while PD was increased from 2.2 to 2.8. Sodium hydroxide loading slightly decreased $M_n$ and $M_w$ and increased PD (Table 2), but these effects were not statistically significant (p-value>0.05).

TABLE 2

| Temperature ° C. | NaOH mg/g dry roots | $M_n$ (×$10^6$) g/mol | $M_w$ (×$10^6$) g/mol | Polydispersity PD |
|---|---|---|---|---|
| 25 | 33 | 0.76 ± 0.22 | 1.55 ± 0.22 | 2.14 ± 0.33 |
| 25 | 66 | 0.66 ± 0.08 | 1.50 ± 0.21 | 2.28 ± 0.18 |
| 25 | 132 | 0.71 ± 0.03 | 1.47 ± 0.09 | 2.07 ± 0.20 |
| 70 | 33 | 0.62 ± 0.07 | 1.41 ± 0.10 | 2.30 ± 0.10 |
| 70 | 66 | 0.57 ± 0.05 | 1.35 ± 0.04 | 2.40 ± 0.17 |
| 70 | 132 | 0.56 ± 0.00 | 1.36 ± 0.04 | 2.41 ± 0.08 |
| 120 | 33 | 0.61 ± 0.02 | 1.41 ± 0.04 | 2.31 ± 0.09 |
| 120 | 66 | 0.50 ± 0.02 | 1.29 ± 0.01 | 2.59 ± 0.07 |
| 120 | 132 | 0.43 ± 0.09 | 1.24 ± 0.11 | 2.90 ± 0.38 |
| 160 | 33 | 0.43 ± 0.02 | 1.09 ± 0.02 | 2.54 ± 0.07 |
| 160 | 66 | 0.40 ± 0.04 | 1.14 ± 0.05 | 2.87 ± 0.18 |
| 160 | 132 | 0.35 ± 0.02 | 1.04 ± 0.04 | 2.97 ± 0.10 |
| Control | | 0.35 ± 0.07 | 1.43 ± 0.04 | 2.26 ± 0.20 |

Number average molecular weight ($M_n$), weight average molecular weight ($M_w$), and polydispersity (PD = $M_w/M_n$) of TK NR as a function of reaction temperature and NaOH loading.
Control treatment was conducted using non-pretreated roots.
Each value is the mean of 3+ standard deviation.

The interaction between reaction temperature and NaOH loading was significant (p-value<0.05) (Table 2). The effect of reaction temperature and NaOH loading on $M_n$ can be roughly divided into two groups: treatments producing NR with $M_n$ lower than, and with Mu greater than 0.6×$10^6$ g/mol. The treatments producing rubber with higher $M_n$ were the control group, those with reaction temperature at 25° C., and those with NaOH loadings of 33 mg NaOH/g TK roots and reaction temperatures of 70° C. and 120° C. (See FIG. 12.) The rest of the treatments produced NR with $M_n$ lower than 0.6×$10^6$ g/mol. The rubbers with the highest and the lowest $M_n$, of 0.7 and 0.3×$10^6$ g/mol, respectively, were obtained from pretreatment conditions at 25° C. and 33 mg NaOH/g TK roots, and 160° C. and 132 mg NaOH/g TK roots, respectively. Rubber $M_w$ in rubber produced by treatments with reaction temperatures lower than 120° C. was not significantly different to control treatments (1.43±0.06×$10^6$ g/mol). However, $M_w$ in treatments at 160° C. was significantly lower than most of the treatments, except for the treatments at 120° C. and NaOH loadings of 66 and 132 mg NaOH/g TK roots (1.16±0.10×$10^6$ g/mol) (Table 2). The treatments of 25° C. and 160° C. and NaOH loadings of 33 and 132 mg NaOH/g TK roots, respectively, had the highest (1.5×$10^6$ g/mol) and smallest $M_w$ (1.0×$10^6$ g/mol), respectively. (See FIG. 13.) PD ranged from 2.1 for rubber from 25° C. and 132 mg NaOH/g TK pretreated roots, to 3.0 for rubber from roots pretreated at 160° C. and 132 mg NaOH/g TK. Rubber with the lowest PDs were obtained from the control treatment (2.2±0.1), pretreatments with the lowest reaction temperature (25° C.), and those with NaOH loading of 33 mg NaOH/g TK roots and reaction temperatures of 70° C. and 120° C. Overall, the results showed that increasing the severity of the alkaline pretreatments lowered rubber molecular weight and increased polydispersity. This has a direct impact on TK NR quality as the quality is directly related to the molecular mass. High molecular weight rubber consistently displays superior physical and mechanical properties and is thus considered higher quality. (Johnson, 1948; Gao et al., 2015; Gentekos et al., 2019; Westall, 1968; Subramaniam, 1972).

2.3. Thermal Properties

Figures 16A, 16B:
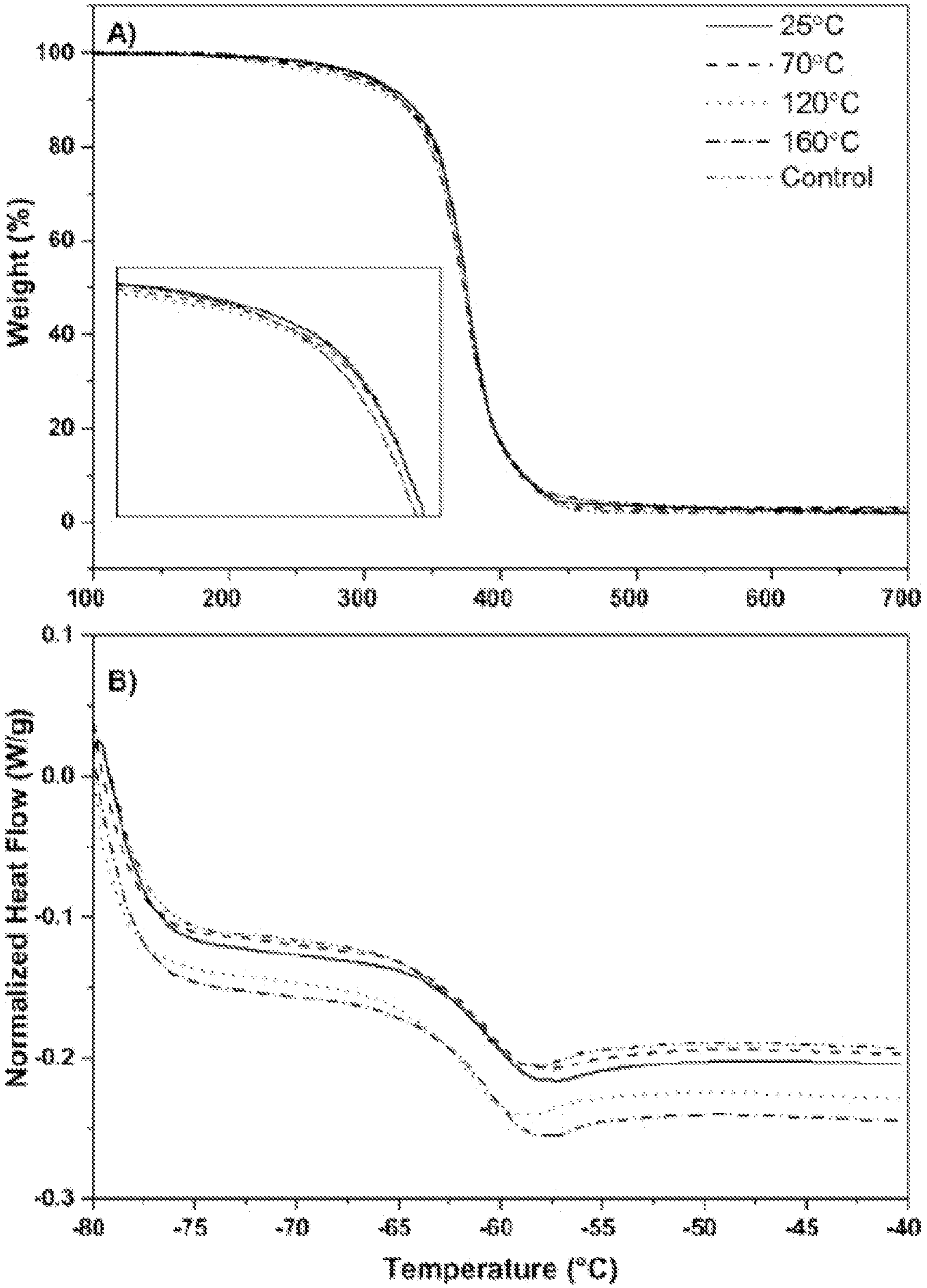
FIGS. 16A-16B show (FIG. 16A) thermogravimetric analysis (TGA) and (FIG. 16B) differential scanning calorimetry (DSC) of crude TK NR obtained by control treatment and alkaline pretreatment at 25° C., 70° C., 120° C., and 160° C., and a sodium hydroxide loading of 66 mg NaOH/g TK. Control treatment was conducted using non-pretreated roots.

TGA for the crude TK NR samples showed a simple decomposition step (FIG. 16A) and only one peak in the derivative curve. Four thermal events were characterized as a function of pretreatment, the water weight loss, the calculated weight loss onset temperature (T0) and the midpoint of the dry weight loss curve (D1/2) and the temperature at the maximum rates of decomposition (MRDT). The mass of the remaining residue, or unvolatilized mass, was also measured. Below 100° C., a weight loss of less than 1% was observed which was attributed to the release of water (Table 3). T0 is a calculated value that denotes the temperature at which dry weight loss begins. It occurred at temperatures of from 340° C. to 348° C. The weight loss that had occurred at these temperatures ranged from 16% to 19% w/w (Table 3). In general, the extrapolated onset temperature (T0) and the weight loss observed at T0, declined with pretreatment temperature (FIG. 16A and Table 3). The third thermal event, D1/2, occurred over a temperature range of from 368 to 375° C. (Table 3). The MRDT ranged from 370° C. to 379° C. (Table 3). The weight of the final residue, measured at 575° C., was from 1.4% to 3.2% w/w (Table 3). The amount of final residue tended to increase with pretreatment NaOH loading rate (Table 3).

TABLE 3

Glass transition temperature ($T_g$) by DSC and thermal events of TGA, of TK NR as a function of reaction temperature and NaOH loading. Control treatment was conducted using non-pretreated roots.

| Temp. ° C. | NaOH mg NaOH/g dry roots | $T_g$ ° C. | Weight loss at 100° C. % w/w crude rubber | Onset T ° C. | Weight loss at Onset T % w/w crude rubber | D1/2 ° C. | MRDT ° C. | FR % w/w crude rubber |
|---|---|---|---|---|---|---|---|---|
| 25 | 33 | −61.6 | 99.8 | 347.9 | 17 | 373.5 | 374.6 | 2 |
| | 66 | −61.5 | 99.7 | 347.4 | 18.6 | 373.2 | 376.5 | 1.7 |
| | 132 | −62.3 | 99.7 | 348.4 | 17.9 | 374.1 | 376.2 | 1.9 |
| 70 | 33 | −62.1 | 99.8 | 348 | 18.3 | 373.2 | 375.25 | 1.9 |
| | 66 | −61.7 | 99.9 | 348.3 | 17.6 | 374.5 | 376.6 | 2.3 |
| | 132 | −62.1 | 99.8 | 348.4 | 18.2 | 374.4 | 377.5. | 2.8 |
| 120 | 33 | −62.1 | 99.9 | 340 | 18 | 368.5 | 370.7 | 1.4 |
| | 66 | −62.5 | 99.7 | 348.5 | 17.3 | 374.8 | 378.6 | 2 |
| | 132 | −62.7 | 99.8 | 344.1 | 17.5 | 372.2 | 375.4 | 3.2 |
| 160 | 33 | −62.8 | 99.9 | 348.4 | 18.1 | 374.7 | 377.2 | 0.8 |
| | 66 | −61.7 | 100 | 343.5 | 16.9 | 372 | 374.2 | 3.1 |
| | 132 | −61.3 | 99.9 | 347.9 | 16.2 | 373.7 | 376 | 2.4 |
| Control | | −62.3 | 99.8 | 349.1 | 18.9 | 374.7 | 376.1 | 2.1 |

The glass transition temperatures ($T_g$) were not significantly different between and within treatments (pooled mean −62.2° C.) nor different from the control ($T_g$=−62.3° C.).

2.4. FTIR Analysis

To analyze the natural rubber extracted and to characterize the effect of the alkaline pretreatments, FTIR and second derivative FTIR spectra were examined.

The crude TK NR samples obtained by both alkaline pretreatment and the control treatments showed characteristic peaks of cis-1,4 polyisoprene as well as small peaks characteristic of non-isoprenoid components, including proteins and lipids (FIGS. 17, 23 and 24A-24B), similar to those found in FTIR of Hevea NR. (Ramirez-Cadavid et al., 2017; Musto et al., 2016; Ramirez-Cadavid et al., 2019.) Peaks at 3280, 1630, and 1540 $cm^{-1}$ associated with amines, and amides I and II, respectively (Lu et al., 1987; Rolere et al., 2015), are characteristic of proteins and were observed in all of the TK NR samples (FIGS. 17, 23 and 24A-24B). Bands at 1711 $cm^{-1}$ and 1748-1738 $cm^{-1}$ characteristic of lipids (Rolere at al., 2015), were also found in the TK NR samples (FIGS. 17, 23 and 24A-24B).

Figure 17:
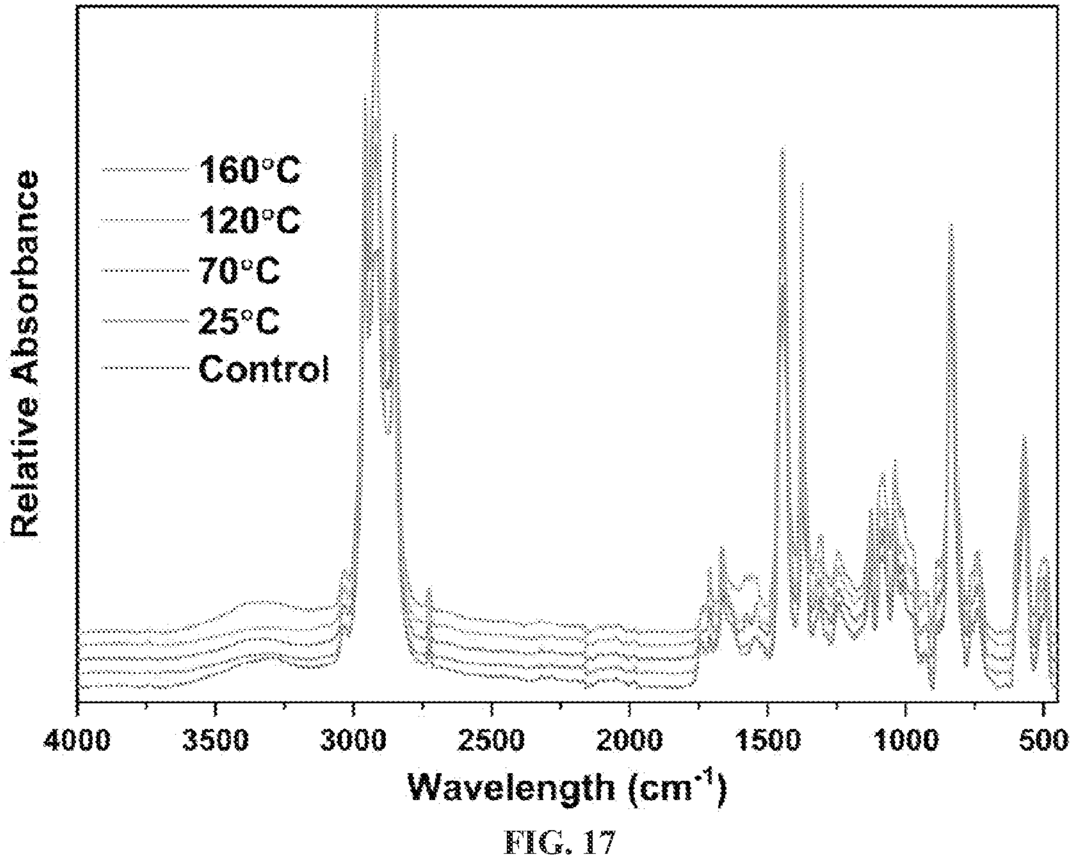
FIG. 17 shows the FTIR spectrum of crude TK NR obtained by control treatment and alkaline pretreatments at 25° C., 70° C., 120° C., and 160° C., and a sodium hydroxide loading of 66 mg NaOH/g TK. Control treatment was conducted using non-pretreated roots.
Figure 23:
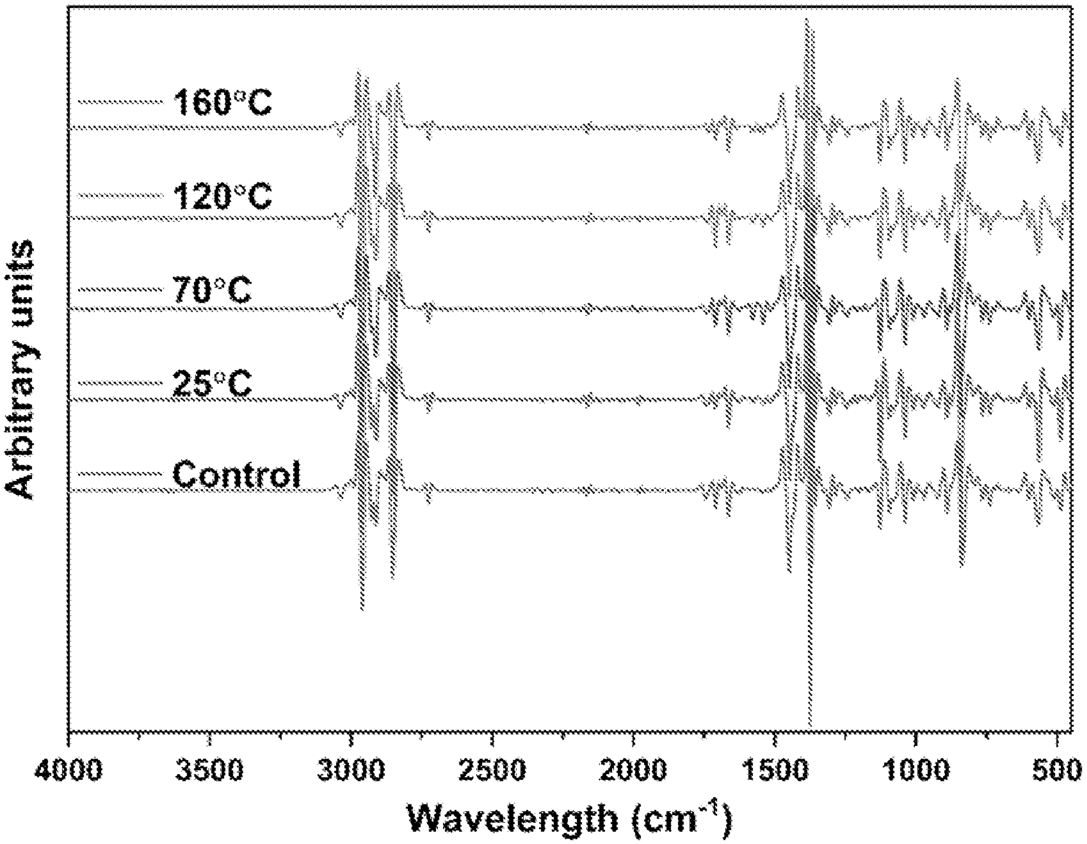
FIG. 23 shows second order derivative of FTIR-UATR spectrum of crude TK NR obtained by control treatment and alkaline pretreatments at 25° C., 70° C., 120° C. and 160° C., and a sodium hydroxide loading of 66 mg NaOH/g TK. Control treatment was conducted using non-alkaline pretreated roots.
Figures 24A, 24B:
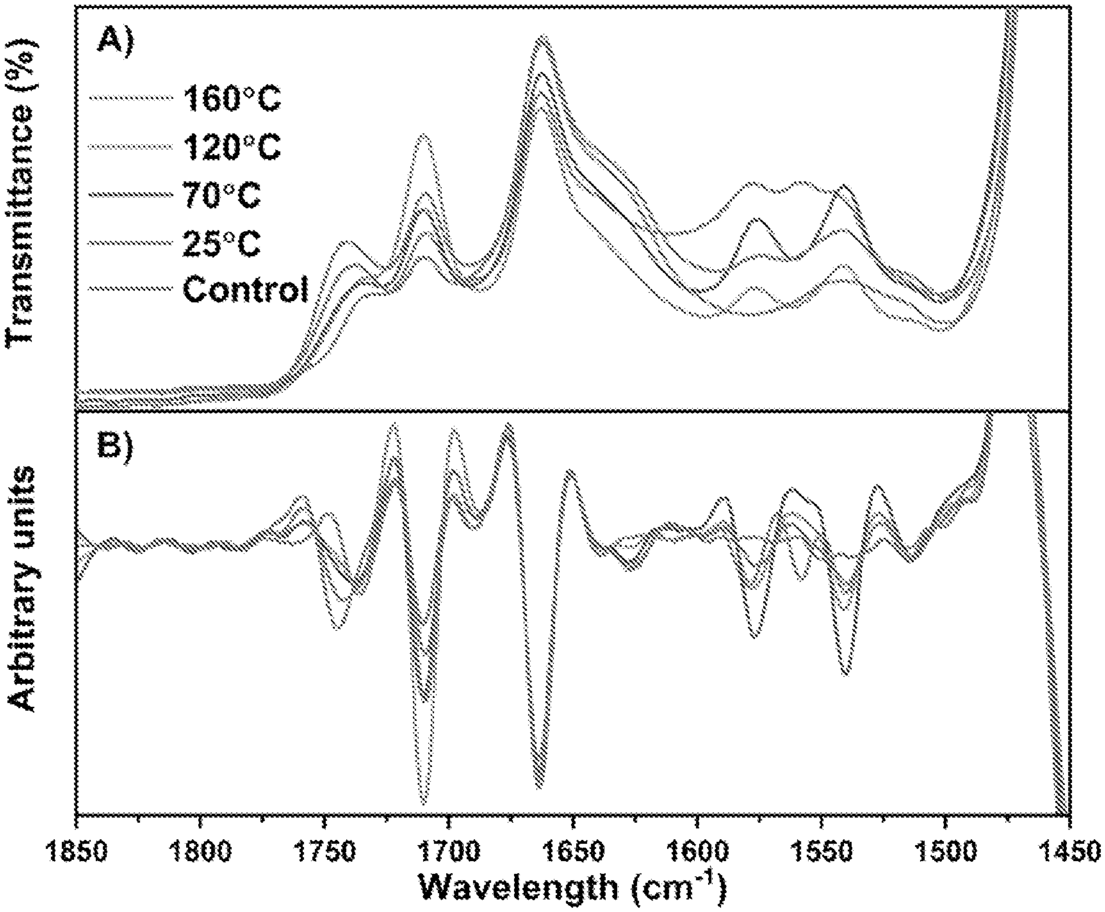
FIGS. 24A-24B show the bands of TK NR non-isoprene components between 1850 $cm^{-1}$ to 1450 $cm^{-1}$ wavelength region, (FIG. 24A) FTIR-UATR, and (FIG. 24B) second order derivative. Crude TK NR was obtained by alkaline pretreatments at 25° C., 70° C., 120° C. and 160° C., and a sodium hydroxide loading of 66 mg NaOH/g TK, and control treatment. Control treatment was conducted using non-pretreated roots.

FTIR of the control unpretreated NR showed carboxyl, ester and amide II characteristic peaks at 1709, 1740, and 1538 $cm^{-1}$, respectively, but the amide II peak was wide indicating the presence of multiple compounds (FIG. 17). The carboxyl, ester and amide II peaks were visible in the second derivative FTIR. An amide II high intensity peak was observed at 1514 $cm^{-1}$ and low intensity peaks were observed at 1547 and 1515 $cm^{-1}$ (FIGS. 23 and 24A-24B). An amide I peak was also clearly visible around 1625 $cm^{-1}$ in the second derivative, but not in the FTIR spectra itself (FIGS. 23 and 24A-24B).

FTIR of alkaline pretreated TK NR samples showed a peak around 1709 $cm^{-1}$ characteristic of carboxyl groups in both FTIR spectra and its second derivative, however, the intensity of this peak changed from sample to sample without a distinguishable trend (FIGS. 17, 23 and 24A-24B). IK NR from these treatments had ester peaks shifted to lower wavelengths at lower intensities as reaction temperate increased (FIGS. 17, 23 and 24A-24B). The Amine I peak at 1630 $cm^{-1}$ was barely visible in the FTIR spectra (FIGS. 17, 24A), but was detectable in the FTIR spectra second derivative. The size of this peak decreased with increasing reaction temperature (FIGS. 17, 23 and 24A-24B). The Amine I peak was absent from FTIR of samples pretreated at 160° C. TK NR obtained from alkaline pretreated roots showed multiple peaks in the amide II region in both the FTIR spectra and its second derivative (FIGS. 17, 23 and 24A-24B). Rubber obtained at pretreatment temperatures of 25° C., 70° C., and 120° C. showed three peaks at 1575, 1540, and 1515 $cm^{-1}$, characteristic of amide II while rubber obtained at a reaction temperature of 160° C. showed these plus an additional peak at 1558 $cm^{-1}$.

2.5. SEM of TK NR and Rubber Impurities

Figure 15:
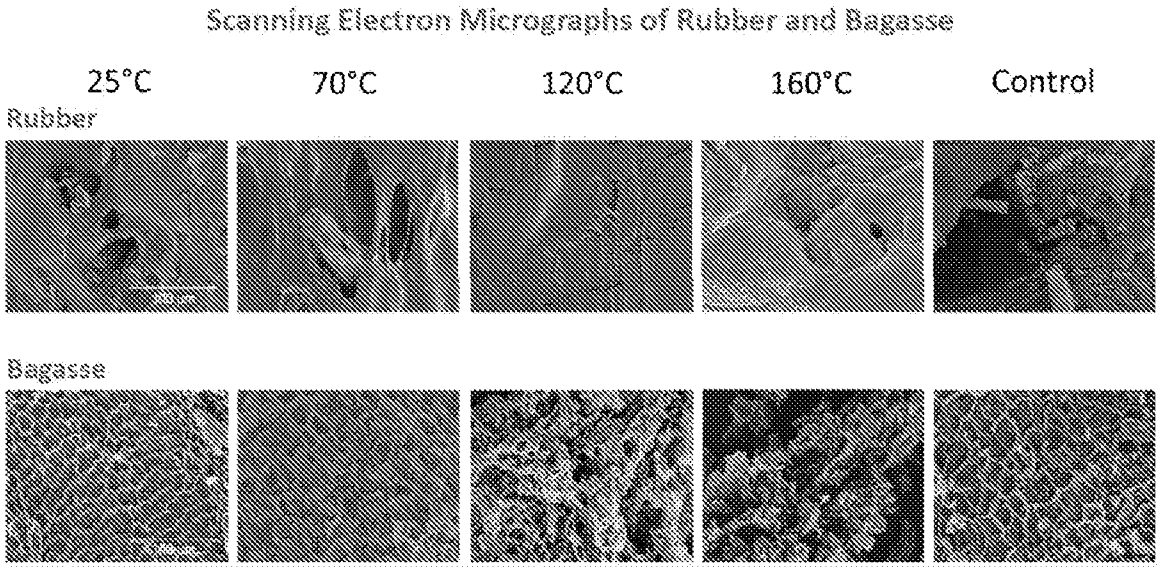
FIG. 15 shows SEM micrographs of crude TK NR and rubber impurities obtained by control treatment and alkaline pretreatments at 25° C., 70° C., 120° C., and 160° C., and a sodium hydroxide loading of 66 mg NaOH/g TK. Control treatment was conducted using non-pretreated roots. Row 1: SEM images of crude NR; Row 2: SEM of separated impurity material.
Figure 18:
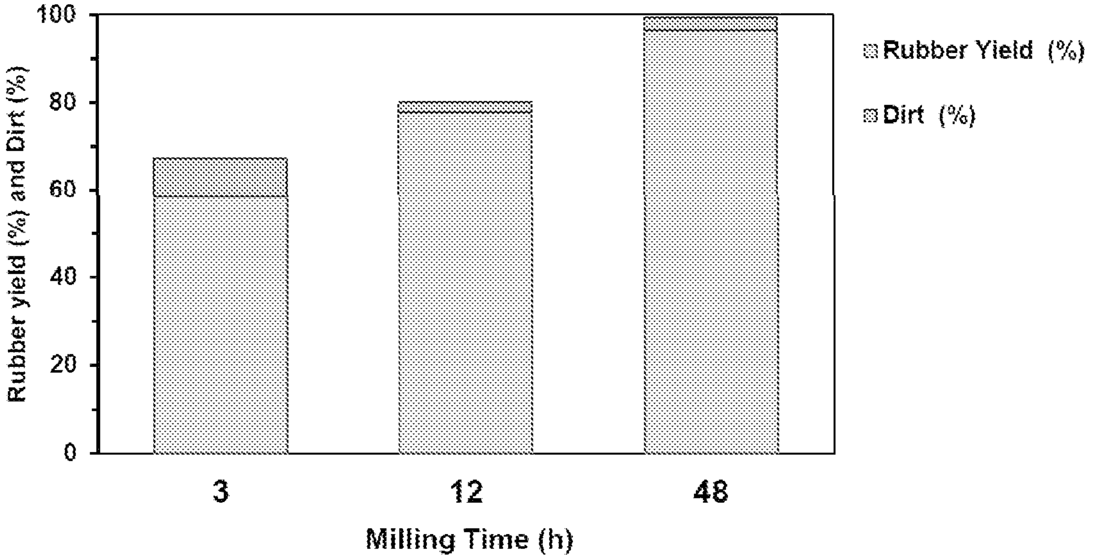
FIG. 18 shows rubber yield (%) and purity (%) at 3 hours of milling time, 12 hours of milling time, and 48 hours of milling time for the Eskew process.
Figure 19:
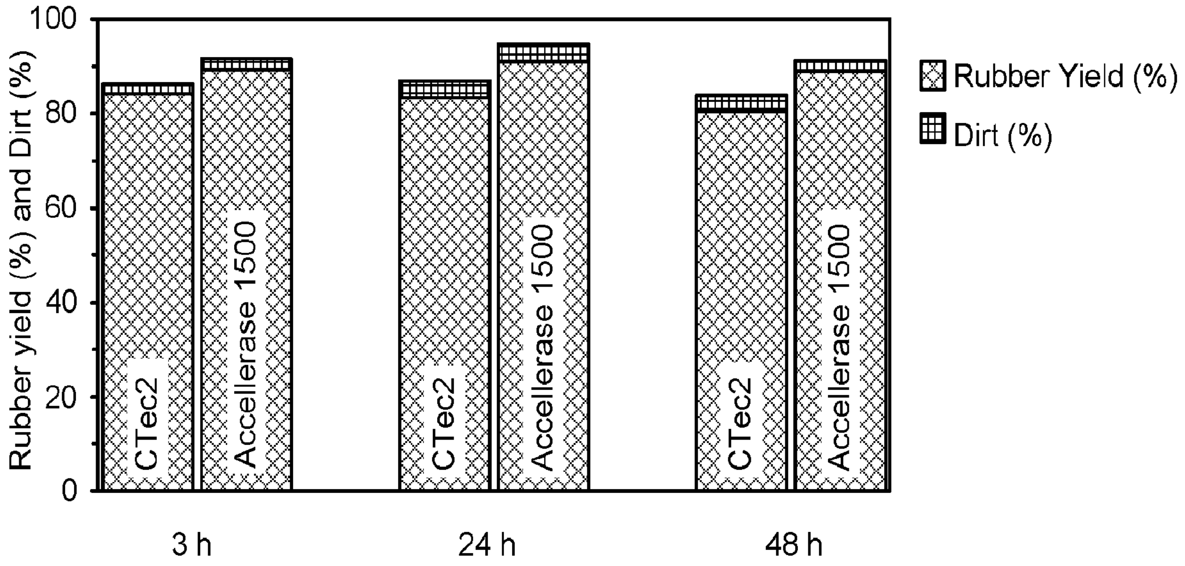
FIG. 19 shows rubber yield (%) and purity (%) at 3 hours of milling time, 12 hours of milling time, and 48 hours of milling time for the PENRA V process with the CTec2 enzyme and the Accellerase 1500 enzyme.

Scanning electron microscopy (SEM) was used to visualize rubber and impurities in alkaline pretreated NR. The appearance of the rubber itself was similar among all the treatments. However, some residual root tissue was observed in the crude TK NR recovered from all treatments (FIG. 18). SEM images of these impurities in the control treatment showed well-defined plant cell wall structures. As pretreatment temperature increased, these cell wall structures tended to disintegrate. In samples pretreated at temperatures of 120° C. and 160° C., total disintegration of cell wall structural components was observed (FIG. 15, row 2).

3. Discussion

Herein, the effects of alkaline pretreatments of TK roots, under a range of temperatures and NaOH concentrations, on natural rubber yield, purity and quality were investigated.

Alkaline pretreatment was used on TK roots after inulin extraction and was followed by enzymatic digestion. This significantly increased TK NR yield compared to unpretreated controls. Rubber yields increased dramatically as sodium hydroxide increased at pretreatment temperatures of 120'° C. and 160° C. (Table 1). At lower temperatures (70° C. and 25° C.), the rubber yields only slightly increased as a function of NaOH loading rate (Table 1). The greater yields of rubber at the more severe alkaline pretreatment conditions (greater severity) could have been caused by degradation of structural carbohydrates (cellulose and hemicellulose) and lignin. This agrees with previous studies, wherein severity was positively corelated with biomass degradation (Silverstein et al., 2007; Garcia-Torreiro et al., 2016). The solubilization of the lignocellulosic fraction of TK roots allows separation of the rubber from other root components (bagasse) during the centrifugation step of the process. SEM analysis of rubber impurities indicated that at the higher pretreatment temperatures, TK root cell wall structures disintegrated (FIG. 15), which is similar to effects observed in other studies of alkaline pretreatment of lignocellulosic biomass (Karp et al., 2014; Karp et al., 2015).

The finding that the impurities observed in the pretreated rubber (Table 1) were more degraded indicates that they were entrapped in the rubber after the pretreatment step especially since the amount of impurities was not significantly affected (Table 1).

The positive impact of alkaline pretreatment on TK rubber yield was offset by a negative effect on rubber molecular mass and gel content (Tables 1 and 2). The $M_n$ and $M_w$ were reduced as pretreatment temperature increased (Table 2). However, there was no impact on molecular mass at a pretreatment temperature of 25° C. (Table 2). The increase in polydispersity (PD) indicated that not all molecules were degraded synchronously.

The reduction in NR quality with alkaline pretreatment at the higher temperatures demonstrates that such pretreatments may not be suitable for TK NR extraction. Low temperature treatments (<70° C.) may be practical for the extraction of the rubber as these treatments significantly increased yield without compromising rubber quality. However, the long-term stability (aging) of alkaline pretreated NR should be further evaluated.

FTIR spectra and its second derivative (FIGS. 17, 23, and 24A-24B) of extracted rubber showed that the bands associated with non-polyisoprene components changed substantially as a result of alkaline pretreatment. Alkaline pretreatment at temperatures greater than or equal to 120° C. increased the intensity and number of bands characteristic of proteins, including amides I and II. Non-polyisoprene components of Hevea NR are part of a network that connects polyisoprene polymer chains and to some degree is responsible for the high molecular weight of natural rubber (Xu et al., 2015; Amnuaypornsri et al., 2008; Toki et al., 2008). The interaction of polyisoprene, proteins and phospholipids at polymer ends is related to rubber gel formation (Sakdapipanich et al., 2012). The reaction of these non-rubber components and their interactions with polyisoprene may have led to the observed reductions in NR molecular mass caused by alkali pretreatment.

Thermal properties of NR were not significantly affected by alkaline pretreatment. This suggests that the reduction in molecular mass and the changes in non-polyisoprene components observed in SEM and FTIR were not severe enough to impact these properties. However, further analysis of DSC measurements indicated that the intensity of the glass transition (step height ΔCp) increased in the rubber pretreated at 160° C. Low molecular weight species in the more polydisperse pretreated samples could be responsible for this behavior. This observation is supported by the higher weight loss percentage at the calculated onset temperature (T0) and the molecular masses of the rubber obtained by alkaline pretreatment at 160° C. compared to the control (FIG. 16A and Table 2, respectively). Overall, the results demonstrated that alkaline pretreatment of TK roots significantly improved rubber yield by solubilizing the lignocellulosic fraction of the roots, while simultaneously reducing TK NR molecular mass and slightly affecting NR thermal properties. It appeared that alkaline pretreatment effects on the molecular and thermal properties of TK NR were also the result of changes to protein, carbohydrate and other components within the rubber. The properties of NR that make it superior to synthetic rubber, are in part attributable to these protein and other constituents, and so their degradation is undesirable. On the other hand, high rubber yield from this alternative source is also desirable, so ways to protect both polyisoprene, protein and other components during alkaline pretreatment is one logical step forward for future research. Antioxidants used in the rubber industry to prevent rubber degradation during rubber production, storage, and processing may be useful in this regard

4. Conclusions

These results indicate that the aqueous extraction of natural rubber from the roots of TK were enhanced by alkaline pretreatment. The process recovered more than 80% of the rubber which is significantly greater than the amount recovered using methods reported in previously.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

REFERENCES

L. Xu, C. Huang, M. Luo, W. Qu, H. Liu, Z. Gu, L. Jing, G. Huang, J. Zheng, A rheological study on non-rubber component networks in natural rubber, RSC Adv. 5 (2015) 91742-91750.

S. Amnuaypornsri, J. Sakdapipanich, Y. Tanaka, Highly purified natural rubber by saponification of latex: analysis of green and cured properties, J. Appl. Polym. Sci. 118 (2010) 3524-3531.

S. Amnuaypornsri, J. Sakdapipanich, S. Toki, B. S. Hsiao, N. Ichikawa, Y. Tanaka, Strain-induced crystallization of natural rubber: effect of proteins and phospholipids, Rubber Chem. Technol. 81 (2008) 753-766.

K. Cornish, Alternative natural rubber crops: why should we care? Technol. Innov. 18 (2017) 245-256.

J. B. van Beilen, Y. Poirier, Guayule and Russian dandelion as alternative sources of natural rubber, Crit. Rev. Biotechnol. 27 (2007) 217-231.

J. B. Van Beilen, Y. Poirier, Production of renewable polymers from crop plants, Plant J. 54 (2008) 684-701.

A. Ahrends, P. M. Hollingsworth, A. D. Ziegler, J. M. Fox, H. Chen, Y. Su, J. Xu, Current trends of rubber plantation expansion may threaten biodiversity and livelihoods, Glob. Environ. Change 34 (2015) 48-58.

K. Cornish, S. K. McNulty, N. Amstutz, A. M. Chanon, S. Walker, M. D. Kleinhenz, A. R. Miller, J. G. Streeter, S. L. Kopicky, Temporal diversity of *Taraxacum kok-saghyz* plants reveals high rubber yield phenotypes, Biodiversitas 17 (2016) 847-856.

M. Kreuzberger, T. Hahn; S. Zibek, J. Schiemann, K. Thiele, Seasonal pattern of biomass and rubber and inulin of wild Russian dandelion (*Taraxacum koksaghyz* L. Rodin) under experimental field conditions, Eur. J. Agron. 80 (2016) 66-77.

M. Arias, J. Herrero, M. Ricobaraza, M. Hernandez, E. Ritter, Evaluation of root biomass, rubber and inulin contents in nine *Taraxacum koksaghyz* Rodin populations, Ind. Crops Prod. 83 (2016) 316-321.

D. A. Ramirez-Cadavid, K. Cornish, F. C. Michel Jr., *Taraxacum kok-saghyz* (TK): compositional analysis of a feedstock for natural rubber and other bioproducts, Ind. Crops Prod. 107 (2017) 624-640.

M. Arias, M. Hernandez, N. Remondegui, K. Huvenaars, P. van Dijk, E. Ritter, First genetic linkage map of *Taraxacum koksaghyz* Rodin based on AFLP, SSR, COS and EST-SSR markers, Sci. Rep. 6 (2016) 31031.

A. Stolze, A. Wanke, N. van Deenen, R. Geyer, D. Prüfer, C. S. Gronover, Development of rubber-enriched dandelion varieties by metabolic engineering of the inulin pathway, Plant Biotechnol. J. 15 (2017) 740-753.

Y. Ikeda, P. Junkong, T. Ohashi, T. Phakkeeree, Y. Sakaki, A. Tohsan, S. Kohjiya, K. Cornish, Strain-induced crystallization behaviour of natural rubbers from guayule and rubber dandelion revealed by simultaneous time-resolved WAXD/tensile measurements indispensable function for sustainable resources, RSC Adv. 6 (2016) 95601-95610.

S. Musto, V. Barbera, M. Maggio, M. Mauro, G. Guerra, M. Galimberti, Crystallinity and crystalline phase orientation of poly(1,4-cis-isoprene) from *Hevea brasiliensis* and *Taraxacum kok-saghyz*, Polymers for Advanced Technologies, (2016) n/a-n/a.

D. A. Ramirez-Cadavid, K. Cornish, U. Hathwaik, R. Kozak, C. McMahan, F. C. Michel Jr., Development of novel processes for the aqueous extraction of natural rubber from *Taraxacum kok-saghyz* (TK), J. Chem. Technol. Biotechnol. 94 (2019) 2452-2464.

Y. Huang, H. Mouri, M. Beaulieu, Processes for the removal of rubber from TKS plant matter. US patent application U.S. Ser. No. 15/007,3113 A1, USPTO, 2015.

R. K. Eskew, Natural rubber from russian dandelion, Rubber Chem. Technol. 19 (1946) 856-864.

P. Stamberger, R. K. Eskew, R. S. Hanslick, Treatment of rubber. U.S. Pat. Nos. 2,399,156 A, 2,399,156 A, 1946.

A. U. Buranov, Process for recovering rubber from rubber-bearing plants with a gristmill. U.S. Pat. No. 7,540,438 B2, USPTO, 2009.

J. Wade, D. Swiger, Dandelion processes, compositions and products. U.S. patent application Ser. No. 13/068,283, USPTO, 2013.

D. A. Ramirez-Cadavid, S. Valles-Ramirez, K. Cornish, F. C. Michel Jr., Simultaneous quantification of rubber, inulin, and resins in *Taraxacum kok-saghyz* (TK) roots by sequential solvent extraction, Ind. Crops Prod. 122 (2018) 647-656.

K. C. Baranwal, H. L. Stephens, Basic Elastomer Technology Rubber division, American Chemical Society, Akron, Ohio, 2001.

ASTM, ASTM D2227-96 Standard Specification for Natural Rubber (NR) Technical Grades, (2015).

A. Limayem, S. C. Ricke, Lignocellulosic biomass for bioethanol production: current perspectives, potential issues and future prospects, Prog. Energy Combust. Sci. 38 (2012) 449-467.

S. Kim, M. T. Holtzapple, Effect of structural features on enzyme digestibility of corn stover, Bioresour. Technol. 97 (2006) 583-591.

R. A. Silverstein, Y. Chen; R. R. Sharma-Shivappa, M. D. Boyette, J. Osborne, A comparison of chemical pretreatment methods for improving saccharification of cotton stalks, Bioresour. Technol. 98 (2007) 3000-3011.

I. Kim, J.-I. Han, Optimization of alkaline pretreatment conditions for enhancing glucose yield of rice straw by response surface methodology, Biomass Bioenergy 46 (2012) 210-217.

E. M. Karp, B. S. Donohoe, M. H. O'Brien, P. N. Ciesielski, A: Mittal, M. J. Biddy, G. T. Beckham, Alkaline pretreatment of corn stover: bench-scale fractionation and stream characterization, ACS Sustain. Chem. Eng. 2 (2014) 1481-1491.

B. L. Johnson, Effect of molecular-weight distribution on physical properties of natural and synthetic polymers, Rubber Chem. Technol. 21 (1948) 654-666.

T. Gao, R. Xie, L. Zhang, H. Gui, M. Huang, Use of rubber process analyzer for characterizing the molecular weight parameters of natural rubber, Int. J. Polym. Sci. 2015 (2015), 517260.

D. T. Gentekos, R. J. Sifri, B. P. Fors, Controlling polymer properties through the shape of the molecular-weight distribution, Nature Reviews, Materials 4 (2019) 761-774.

B. Westall, The molecular weight distribution of natural rubber latex, Polymer 9 (1968) 243-248.

A. Subramaniam, Gel. permeation chromatography of natural rubber, Rubber Chem. Technol. 45 (1972) 346-358.

American Society for Testing and Materials, ASTM D1278-91a, 2015. standard test methods for rubber from natural sources-Chemical analysis, ASTM International. West Conshohocken, PA, 2015.

ISO/DS 17278, Determination of gel content for technically specified rubber, TSR, International Organization for Standardization (ISO), 2012.

R. P. Overend, E. Chornet, J. A. Gascoigne, Fractionation of lignocellulosics by steam-aqueous pretreatments, Philos. Trans. R. Soc. Lond. Ser. A Math. Phys. Sci. 321 (1987) 523-536.

H. L. Chum, D. K. Johnson, S. K. Black, R. P. Overend, Pretreatment-catalyst effects and the combined severity parameter, Appl. Biochem. Biotechnol. 24 (1990) 1.

F. J. Lu, S. L. Hsu, A vibrational spectroscopic analysis of the structure of natural rubber, Rubber Chem. Technol. 60 (1987) 647-658.

S. Rolere, S. Liengprayoon, L. Vaysse, J. Sainte-Beuve, F. Bonfils, Investigating natural rubber composition with Fourier Transform Infrared (FT-IR) spectroscopy: a rapid and non-destructive method to determine both protein and lipid contents simultaneously, Polym. Test. 43 (2015) 83-93.

M. Garcia-Torreiro, M. A. Pallin, M. López-Abelairas, T. A. Lu-Chau, J. M. *Lema*, Alkali treatment of fungal pretreated wheat straw for bioethanol production, Bioethanol 2 (2016).

E. M. Karp, M. G. Resch, B. S. Donohoe, P. N. Ciesielski, M. H. O'Brien, J. E. Nill, A. Mittal, M. J. Biddy, G. T. Beckham, Alkaline pretreatment of switchgrass, ACS Sustain. Chem. Eng. 3 (2015) 1479-1491.

S. Toki, C. Burger, B. S. Hsiao, S. Amnuaypornsri, J. Sakdapipanich, Y. Tanaka, Multi-scaled microstructures in natural rubber characterized by synchrotron X-ray scattering and optical microscopy, POLB J. Polym. Sci. Part B Polym. Phys. 46 (2008) 2456-2464.

J. Sakdapipanich, P. Rojruthai, Molecular structure of natural rubber and its characteristics based on recent evidence, biotechnology in: R. Sammour (Ed.) Molecular Studies and Novel Applications for Improved Quality of Human Life, In Tech2012.

What is claimed is:

1. A method of purifying rubber from *Parthenium argentatum* (Guayule bush) or *Taraxacum kok-saghyz* (Russian dandelion), a, the method comprising:

a) contacting plant material with hot water or a dilute basic aqueous solution, thereby forming a plant material composition with a concentration of 3% or less of water extractable materials by weight and an inulin-containing composition;

b) separating the plant material composition from the inulin-containing composition;

c) pebble milling the plant material composition in the presence of enzymes comprising pectinase, cellulase, and/or hemicellulase;

d) centrifuging the product of step c) at 1 g or greater to separate rubber from other material; and e) removing the rubber;

wherein the method can be completed in less than six hours.

2. The method of claim 1, wherein the pebble milling and addition of enzymes in step b) occur simultaneously.

3. The method of claim 1, wherein no additional water is used during step b).

4. The method of claim 1, wherein the plant material comprises root material.

5. The method of claim 1, wherein step b) further comprises adding a buffer.

6. The method of claim 1, wherein centrifugation is at 1 g or greater.

7. The method of claim 1, wherein centrifugation results in at least three separate fractions, wherein the three separate fractions comprise an upper fraction, a middle fraction, and a lower fraction.

8. The method of claim 7, wherein the upper fraction comprises 95% or more of the rubber from the plant.

9. The method of claim 7, wherein the middle fraction comprises enzymes, monomeric sugars, oligomeric sugars, or any combination thereof and/or the lower fraction comprises bagasse.

10. The method of claim 7, wherein the upper fraction of rubber is separated.

11. The method of claim 7, further comprising washing the upper fraction of rubber and/or further separating the upper fraction of rubber.

12. The method of claim 11, wherein further separating the upper fraction of rubber comprises mechanical separation, chemical separation, or any combination thereof.

13. The method of claim 12, wherein mechanical separation comprises screening, pebble milling, or any combination thereof.

14. The method of claim 1, wherein products other than rubber are extracted and purified.

15. The method of claim 1, further comprising contacting the plant material with an antioxidant.

16. The method of claim 15, wherein the antioxidant comprises primary antioxidants, secondary antioxidants, or any combination thereof.

17. The method of claim 16, wherein primary antioxidants comprise phenolic antioxidants, amine antioxidants, or any combination thereof and/or secondary antioxidants comprise phosphite antioxidants, thioester antioxidants, or any combination thereof.

* * * * *